(12) United States Patent
Suzuki

(10) Patent No.: US 8,133,834 B2
(45) Date of Patent: Mar. 13, 2012

(54) OXIDATION CATALYST

(75) Inventor: Ken Suzuki, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 12/591,266

(22) Filed: Nov. 13, 2009

(65) Prior Publication Data

US 2010/0069670 A1    Mar. 18, 2010

Related U.S. Application Data

(63) Continuation of application No. 10/565,886, filed as application No. PCT/JP2004/010399 on Jul. 22, 2004, now abandoned.

(30) Foreign Application Priority Data

Jul. 25, 2003   (JP) ................................ 2003-279738

(51) Int. Cl.
   B01J 21/00    (2006.01)
   B01J 23/00    (2006.01)
   B01J 25/00    (2006.01)
   B01J 29/00    (2006.01)
   B01J 31/00    (2006.01)

(52) U.S. Cl. ......................... 502/167; 502/100; 502/150

(58) Field of Classification Search .................. 502/167, 502/100, 150
   See application file for complete search history.

(56) References Cited

U.S. PATENT DOCUMENTS 2,966,455 A  *  12/1960  Archibald ................. 208/254 R
3,095,394 A  *   6/1963  McGary, Jr. ................. 524/189

FOREIGN PATENT DOCUMENTS

| EP | 0 962 440 | 12/1999 |
| EP | 1 128 453 | 8/2001 |
| WO | 99/43643 | 9/1999 |

OTHER PUBLICATIONS

Reg Davis et al., A Study of the Mechanism of Alkane Hydroxylation using the $Fepy_4Cl_2$-PhNHNHPh-$O_2$ System, 1987, pp. 425-438.
Ming-De Gui et al., Synthesis and Magnetic and Catalytic Properties of Manganous Isonicotinoyl Hydrazone Complexes, 1998, pp. 1381-1391.
J. Bretschneider et al., Über Stabile Ein-, Zwei- Und Drei-Wertige Hydrazyle Der Cyanckohlenstoffreihe, Tetrahedron vol. 24, No. 3, 1968; pp. 1063-1081, Abstract.
Supplementary European Search Report issued on Oct. 13, 2009 in corresponding European Patent Application No. 04747810.
U.S. Appl. No. 10/565,886, filed Jan. 25, 2006 Ken Suzuki, Asahi Kasei Chemicals Corporation.

* cited by examiner

Primary Examiner — James McDonough
(74) Attorney, Agent, or Firm — Staas & Halsey LLP

(57) ABSTRACT

An oxidation catalyst for use in the oxidation of a substrate with a molecular oxygen, comprising at least one member selected from the group consisting of a specific hydrazyl radical (such as 2,2-diphenyl-1-picrylhydrazyl) and a specific hydrazine compound (such as 2,2-diphenyl-1-picrylhydrazine). A method for producing a chemical compound, comprising contacting a substrate with a molecular oxygen in the presence of the above-mentioned oxidation catalyst.

25 Claims, No Drawings

US 8,133,834 B2

OXIDATION CATALYST

This application is a continuation of U.S. patent application Ser. No. 10/565,886, filed Jan. 25, 2006 now abandoned, and is based on and hereby claims priority to PCT Application No. PCT/JP2004/010399 filed on Jul. 22, 2004 and Japanese Application No. 2003-279738 filed on Jul. 25, 2003, the contents of which are hereby incorporated by reference.

BACKGROUND OF THE INVENTION

1. Field of the Invention

The present invention relates to an oxidation catalyst useful for chemical synthesis. More particularly, the present invention is concerned with an oxidation catalyst for use in the oxidation of a substrate with a molecular oxygen, comprising at least one member selected from the group consisting of a specific hydrazyl radical and a specific hydrazine compound. By the use of the oxidation catalyst of the present invention, oxidation of a substrate (such as a hydrocarbon, an alcohol, a carbonyl compound, an ether, an amine, a sulfur compound or a heterocyclic compound) with a molecular oxygen can be efficiently performed under moderate conditions, thereby enabling economical production of a useful chemical compound with high selectivity. The present invention is also concerned with a method for producing a chemical compound by using the oxidation catalyst of the present invention.

2. Prior Art

An oxidation reaction is one of the most basic methods for material conversion in the field of organic synthesis. A number of oxidation processes have been put into practical use. However, in many cases of oxidation reactions, for example, oxygen oxidation reactions, there are disadvantages not only in that high temperature and high pressure conditions are necessary for activation of a molecular oxygen, thus leading to a lowering of the selectivity for a desired compound, but also in that, because of the generation of various by-products, it is necessary to perform various separation steps for removing the by-products. Therefore, the conventional oxidation processes are not at a satisfactory technical level from the viewpoint of economy, safety, and environmental protection. Thus, it has been desired to develop a new oxidation process which can be efficiently performed with high selectivity and at a low cost.

Conventionally, oxidation reactions which are well known in the industry, especially a selective oxidation reaction, have been carried out by employing the techniques as described below.

Useful chemical compounds can be efficiently produced under moderate conditions with high selectivity by performing a selective oxidation reaction, using an oxidizing agent (such as hydrogen peroxide or an organic or inorganic peroxide) which can produce an active oxygen species (an electrophilic oxygen species) having high chemical potential (see, for example, "Shin Jikken Kagaku Koza 15, Sanka to Kangen I-2 (New Lecture on Experimental Chemistry 15, Oxidation and Reduction, I-2)", edited by the Japan Chemical Society, p. 605, 1976, Japan; and "Catalytic Oxidations with Hydrogen Peroxide as Oxidant", G. Strukul, Kluwer Academic Publishers, 1992, the Netherlands). Examples of selective oxidation reactions include oxidation of an alkane, oxidation of an alcohol, epoxidation of an olefin, oxidation of a ketone, oxidation of an aldehyde, oxidation of an ether, hydroxylation of an aromatic compound, oxidation of an amine and oxidation of a sulfur compound.

On the other hand, it is well known that, as a conventional method for producing hydrogen peroxide, which is a useful oxidizing agent as mentioned above, an autoxidation reaction using alkylanthraquinone is commercially used (see "Kagaku Binran, Oyo-kagaku-hen I (Chemical Handbook, Applied Chemistry I)", edited by the Japan Chemical Society, p. 302, 1986, Japan). However, the conventional method for producing hydrogen peroxide is economically disadvantageous not only in that the method requires a large amount of an organic solvent, but also in that, due to the generation of various by-products and degradation of a catalyst, the method requires various additional steps for separation of by-products and for regeneration of the degraded catalyst. Therefore, it has been desired to develop a production method by which hydrogen peroxide can be produced at a low cost, as compared to the case of the conventional method.

In addition, as a useful organic peroxide, t-butylhydroperoxide is also known. Conventionally, t-butylhydroperoxide has been produced, for example, by a method in which t-butanol or isobutylene as a substrate, namely a raw material, is reacted with a strong acid, such as sulfuric acid, and hydrogen peroxide (see, for example, "Yuki-Kasankabutsu (Organic Peroxides)", edited by the Organic Peroxide Research Group, p. 220, 1972, Japan). However, the conventional method is disadvantageous from the viewpoint of economy and safety; specifically, the conventional method has disadvantages in that hydrogen peroxide (which is expensive) is necessary, and the raw material is reacted with a liquid mixture of a high concentration aqueous sulfuric acid (60 to 70 wt %) and a high concentration aqueous hydrogen peroxide (30 to 50 wt %).

For these reasons, from the practical and commercial viewpoint, it has been desired to develop a method by which various types of selective oxidation reactions mentioned above can be performed by directly activating and oxidizing a substrate with oxygen in the presence of a catalyst without using an expensive oxidizing agent, such as hydrogen peroxide. For example, a method for producing phenol directly from benzene and oxygen in the presence of a catalyst has long been studied. However, the reaction method which has been studied has the following problems. First, a high temperature is necessary for the reaction. Further, although various types of catalysts can catalyze the reaction, many of such catalysts pose a problem in that the reaction system containing such catalysts causes phenol as a reaction product to have higher reactivity than benzene as a substrate, so that, although the reaction rate of benzene can be increased, the selectivity for phenol is decreased. Thus, the above-mentioned method is not commercially employable. With respect not only to such reaction system (which causes phenol as a reaction product to have higher reactivity than benzene) but also to other oxidation reactions using oxygen, great efforts have been made for increasing the selectivity for a desired reaction product. However, there is no method which is satisfactory from the viewpoint of economy and safety. It is considered that the reason why such an oxidation reaction using oxygen does not proceed with high selectivity for a desired product resides in that, when oxygen molecules are activated by a catalyst, an electron transfer from the catalyst to the oxygen molecules inevitably occurs, so that oxygen molecules are mainly converted to nucleophilic oxygen anion active species, thus rendering it difficult for an electrophilic addition reaction to proceed (see Catalysis Today, 45, 3-12, 1998, the U.S.A.).

In recent years, in order to alleviate the above-mentioned problems, studies on a new method have been made for synthesizing a chemical compound, in which a catalyst system which is similar to a biological catalyst system is used. Monooxygenase, which is an enzyme present in the living body, activates an oxygen molecule by utilizing the reducing ability of NADPH. In imitation of this mechanism, in the synthetic chemistry, a method can be used in which oxygen and a reducing agent, such as hydrogen, carbon monoxide, aldehyde or hydrazine, are contacted with each other in the presence of a catalyst system, thereby generating an active oxygen species stoichiometrically under moderate conditions. In this case, since energy necessary to cleave an oxygen bond is supplied through the oxidation of the reducing agent, an electrophilic active oxygen species can be selectively generated without using a large amount of energy.

There are also known methods similar to such method, such as a method for producing phenol, comprising contacting oxygen, benzene and hydrogen with each other in the presence of a Pt—$V_2O_5$/$SiO_2$ catalyst (Appl. Catal., A, 131, 33, 1995, U.S.A.); a method for producing cyclohexene oxide, comprising contacting oxygen, cyclohexene and hydrogen with each other in the presence of an Mn complex/ Pt colloidal catalyst (J. Am. Chem. Soc., 101, 6456, 1979, U.S.A.); a method for producing cyclohexanone and cyclohexanol, comprising contacting oxygen, cyclohexane and acetoaldehyde with each other in the presence of an $Fe_2O_3$ catalyst in an acetic acid solvent (J. Mol. Catal., A: Chemical, 117, 21, 1979); and a method for producing cyclohexanone and cyclohexanol, comprising contacting oxygen, cyclohexane and 1,2-diphenylhydrazine with each other in the presence of an Fe(pyridine)$_4$Cl$_2$ catalyst (Polyhedron, 7(6), 425, 1988). These methods exhibit an improved selectivity for a desired product. However, each of these methods has problems not only in that the presence of a reducing agent poses a high danger of explosion, but also in that the use efficiency of a reducing agent is low and an oxidation product of a reducing agent is by-produced. Therefore, these methods cannot be commercially practically employed.

On the other hand, as described below, studies are now being performed for developing a new oxidation catalyst which can be used to perform oxidation of various substrates with a molecular oxygen under moderate conditions without using a reducing agent.

There has been proposed a method in which a substrate, such as an alkane, an alcohol or a ketone, is subjected to oxidation with a molecular oxygen by using, as an oxidation catalyst, an imido compound, such as N-hydroxyphthalimide (see, for example, Unexamined Japanese Patent Application Laid-Open Specification No. Hei 10-286467 (corresponding to U.S. Pat. No. 5,981,420 and EP 858835 B1)). In this method, selective oxidation of a substrate can be performed under moderate conditions. However, this method poses problems not only in that the catalyst activity of an imido compound is unsatisfactory, thus rendering it necessary to use the imido compound catalyst in an amount as large as about 10 mole %, based on the molar amount of the substrate, but also in that the imido compound is decomposed and consumed during the reaction, thus increasing the cost of producing a chemical compound by this method.

Also, it is known to use as a catalyst a nitroxyl radical (such as 2,2,6,6-tetramethylpiperidine-N-oxyl (TEMPO)) in a method for selective oxidation of an alcohol (see Chem. Comm., p. 1591, 1999). In this method, an alcohol is converted selectively into a carbonyl compound or the like by using a catalyst comprising a combination of TEMPO and a ruthenium compound. However, this method poses problems in that not only is the catalyst activity unsatisfactory, but also the nitroxyl radical undergoes degradation during the reaction.

As methods in which a metal metalloporphyrin complex or a metallosalen complex is used as a catalyst, there can mentioned, for example, an oxidative acetoxylation reaction of a diene by using a ternary catalyst system of [Pd salt/Co-porphyrin complex/hydroquinone] (see Angew. Chem. Int. Ed. Engl., 32, 263, 1993), a method in which a ternary catalyst system of [Ru complex/Co-salen complex/hydroquinone] is used to perform an oxidation reaction of a primary alcohol to form aldehyde or an oxidation reaction of a secondary alcohol to form a ketone (see J. Chem. Soc., Chem. Commun., p. 1037, 1994), an oxidation reaction of an amine by using an azaindole/copper complex (see "Nihon Kagakukai Dai-67 Shunki Nenkai Kouen Yokou-shu II (the preliminary text II for the lectures at the 67th Spring Annual Meeting of the Chemical Society of Japan), p. 1025, 1994, Japan), an oxidative dehydrogenation reaction of an amine by using a heteropolyacid (see ° Nihon Kagakukai Dai-67 Shunki Nenkai Kouen Yokou-shu II (see the preliminary text II for the lectures at the 67th Spring Annual Meeting of the Chemical Society of Japan), p. 761, 1994, Japan), and an oxidation reaction of an alkane by using iron-disubstituted tungstosilicic acid (Chem. Lett., p. 1263, 1998). However, these methods pose problems not only in that the reaction rate and the selectivity for and yield of a desired chemical compound are not always high, but also in that the catalyst has the following disadvantages: the preparation of the catalyst requires a complicated operation and, hence, the catalyst is expensive, and also the catalyst is unstable and likely to be decomposed during the reaction.

Next, an explanation is made below on the conventional methods for producing an oxime compound, a nitro compound and a nitrone compound which are induced by oxidation of an amine.

Oxime compounds and nitro compounds are important chemical compounds for use as, for example, ordinary and fine chemicals and intermediates for synthesis of pharmaceuticals. Examples of methods for producing an oxime compound by oxidation of a primary amine include a method which uses dimethyl dioxirane as an oxidizing agent (see J. Org. Chem., 57, 6759, 1992), a method which uses hydrogen peroxide as an oxidizing agent and uses a sodium tungsten catalyst (see Angew. Chem., 72, 135, 1960), a method which uses hydrogen peroxide as an oxidizing agent and uses a methyltrioxorhenium catalyst (see Bull. Chem. Soc. Jpn., 70, 877, 1997), and a method which uses hydrogen peroxide as an oxidizing agent and uses a titanium silicalite molecular sieves (TS-1) as a catalyst (see J. Chem. Soc. Perkin Trance. I, 2665, 1993). However, these methods have a problem in that an explosive oxidizing agent (dimethyl dioxirane or hydrogen peroxide) is used or that an expensive oxidizing agent or an expensive catalyst is used. These methods are also disadvantageous in that the catalyst activity is unsatisfactory and the selectivity for and yield of an oxime compound are not always high. Therefore, these methods are commercially unsatisfactory.

Examples of methods for producing a nitro compound by oxidation of a primary amine include a method which uses m-chloroperbenzoic acid or a pertrifluoroacetic acid as an oxidizing agent (see J. Org. Chem., 58, 1372, 1993), a method which uses potassium permanganate as an oxidizing agent (see Org. Synth., 52, 77, 1972), a method which uses ozone as an oxidizing agent (see Synthetic Commun., 20, 1073, 1990), a method which uses t-butylhydroperoxide as an oxidizing agent and uses a catalyst comprising chromium carried on a silica carrier (see J. Chem. Soc. Commun., 1523, 1995), and a method which uses dimethyl dioxirane as an oxidizing agent (see Tetrahedron Lett., 27, 2335, 1986). However, these methods have a problem in that an expensive peroxide, an excess amount of a heavy metal-containing oxidizing agent or an explosive oxidizing agent (such as ozone, an organic hydroperoxide or dimethyl dioxirane) is used. Therefore, these methods are commercially unsatisfactory.

Cyclohexanone oxime, which is an oxime compound, is a chemical compound useful as an intermediate for producing ε-caprolactam which is a raw material for producing nylon-6. Cyclohexanone oxime can be synthesized by reacting a cyclohexyl amine as a raw material with an oxidizing agent. Examples of methods for producing cyclohexanone oxime by using hydrogen peroxide as an oxidizing agent include (1) a method which uses a catalyst containing at least one metal selected from the group consisting of Mo, W and U (see U.S. Pat. No. 2,706,204), (2) a method which uses titanium silicalite or vanadium silicalite as a catalyst (see Tetrahedron, 51(41), 11305, 1995, and Catal. Lett., 28(2 to 4), 263, 1994), and (3) a method which uses a catalyst containing at least one metal selected from the group consisting of Ti, V, Cr, Se, Zr, Nb, Mo, Te, Ta, W, Re and U (see U.S. Pat. No. 3,960,954).

Examples of methods for producing cyclohexanone oxime by using a molecular oxygen as an oxidizing agent include (4) a method in which a gaseous phase reaction is performed using a solid catalyst comprising an $SiO_2$ gel, $\gamma$-$Al_2O_3$ and optionally $WO_3$ (see U.S. Pat. Nos. 4,337,358 and 4,504,681), (5) a method in which a gaseous phase reaction is performed using a solid catalyst comprising a combination of tungsten oxide and one member selected from the group consisting of $\gamma$-$Al_2O_3$, $SiO_2$ and hydrotalcite (see Journal of Molecular Catalysis A; Chemical, 160, 393, 2000), (6) a method in which a liquid phase reaction is performed using, as a catalyst, tungstic acid, phosphotungstic acid, molybdic acid, selenic acid; selenious acid or the like in the presence of a tertiary alcohol, preferably in the presence of a tertiary alcohol and ammonia gas (see Examined Japanese Patent Application Publication No. Sho 47-25324), and (7) a method in which a liquid phase reaction is performed using, as a catalyst, a compound containing at least one element selected from the Group 4 (Ti, Zr and Hf) of the Periodic Table (see EP 395046 B1).

However, these prior art methods have problems. For example, the above-mentioned methods (1) to (3) have problems not only in that the oxidizing agent used (i.e., hydrogen peroxide or an organic hydroperoxide) is expensive, but also in that the selectivity for and yield of the cyclohexanone oxime produced are not always high, and also there is the known operational danger (explosiveness) of the oxidizing agent when the reaction is performed on a commercial scale. In addition, when an organic hydroperoxide is used, there is also a problem in that a by-product generated by reduction of the organic hydroperoxide is contained in the reaction mixture, thus rendering cumbersome the separation and purification operations. For solving these problems, the above-mentioned methods (4) to (7), which use a molecular oxygen (such as air or oxygen gas), have been proposed.

In the above-mentioned methods (4) and (5), the gaseous phase reaction is performed under relatively stringent reaction conditions using a reaction temperature of from 120 to 250° C. In the studies by the present inventors, it has been found that the above-mentioned methods (4) and (5) pose a problem in that, when the reaction temperature is 160° C. or more, a tar-like by-product and a high boiling point organic carbonaceous material accumulate on the surface of the catalyst, thus causing a rapid deactivation of the catalyst. Also, the methods (4) and (5) are disadvantageous in that the selectivity for cyclohexanone oxime is as low as about 50 to 60% at a conversion of 20%, thus causing a lowering of the amount of reaction product per unit volume of the space of reaction, i.e., a lowering of the productivity. In the above-mentioned methods (6) and (7), the gaseous phase reaction is performed under relatively moderate reaction conditions using a reaction temperature of from 50 to 150° C. The prior art document describing the method (6) discloses a reaction in which t-butanol is used as a reaction solvent and phosphotungstic acid is used as a catalyst; however, the method (6) has a problem in that the yield of cyclohexanone oxime is as low as only few percent. The prior art document describing the method (7) discloses a reaction in which a titanium compound is used as a catalyst, and diethylene glycol dimethyl ether (i.e., diglyme), t-butanol, dimethyl formamide, acetonitrile, triethylamine or water is used as a reaction solvent; however, the method (7) has problems in that the selectivity for cyclohexanone oxime is as low as about 30 to 50% and also the catalyst activity is low.

Nitrone compounds, which are induced by oxidation of amines, are important chemical compounds for use as intermediates for synthesis of pharmaceuticals, agrichemicals and fine chemicals, such as an α-substituted amine compound, an amino acid and an alkaloid. As a method for producing a nitrone compound, there is known a method in which a secondary amine is reacted with hydrogen peroxide. Examples of such methods for producing a nitrone compound include a method which uses a sodium tungsten catalyst (see Unexamined Japanese Patent Application Laid-Open Specification No. Sho 59-164762 (corresponding to U.S. Pat. No. 4,596,874)), a method which uses a selenium dioxide catalyst (see Unexamined Japanese Patent Application Laid-Open Specification No. Sho 63-63651), and a method which uses a methyltrioxorhenium catalyst (see Bull. Chem. Soc. Jpn., 70, 877, 1997). However, these methods have problems not only in that hydrogen peroxide (which is expensive) or an expensive catalyst is used, but also in that the catalyst activity is unsatisfactory and the selectivity for and yield of a nitrone compound are not always high. Thus, these methods are unsatisfactory from the commercial viewpoint. There is also known another method for producing a nitrone compound, which uses a molecular oxygen as an oxidizing agent and uses hydrazine (reducing agent) and a flavin catalyst (see J. Am. Chem. Soc., 125, 2868, 2003). This method exhibits a high selectivity for a desired chemical compound; however, this method has problems not only in that hydrazine as a reducing agent is expensive, but also in that the catalyst has disadvantages in that the preparation of the catalyst requires a complicated operation and, hence, the catalyst is expensive. Thus, this method is unsatisfactory from the commercial viewpoint.

As apparent from the above, it has been desired to develop an oxidation method which can be used to produce various desired chemical compounds (for example, to produce an oxime compound or a nitro compound from a primary amine or produce a nitrone compound from a secondary amine) by an oxidation reaction (such as an oxygen oxidation reaction) performed under moderate conditions with high selectivity and high efficiency. It has also been desired to develop a high performance oxidation catalyst used for the oxidation method.

DISCLOSURE OF THE INVENTION

Problems to be Solved by the Invention

Thus, in the prior art, there has not yet been obtained an oxidation catalyst which can be used to efficiently perform oxidation of a substrate (such as a hydrocarbon, an alcohol, a carbonyl compound, an ether, an amine, a sulfur compound or a heterocyclic compound) with a molecular oxygen under moderate conditions, thereby enabling economical production of a useful chemical compound with high selectivity.

Means to Solve the Problems

Summary of the Invention

In this situation, the present inventor has made extensive and intensive studies with a view toward solving the above-mentioned problems. As a result, he has unexpectedly found that, by the use of an oxidation catalyst comprising a specific hydrazyl radical (such as 2,2-diphenyl-1-picrylhydrazyl) and/or a specific hydrazine compound (such as 2,2-diphenyl-1-picrylhydrazine) or by the use of an oxidation catalyst comprising a combination of the above-mentioned hydrazyl radical and/or hydrazine compound with an oxidation promoter (such as a transition metal compound), oxidation of a substrate (such as a hydrocarbon, an alcohol, a carbonyl compound, an ether, an amine, a sulfur compound or a heterocyclic compound) with a molecular oxygen can be performed under moderate conditions, thereby enabling production of a desired chemical compound with high selectivity and high efficiency. The present invention has been completed, based on this finding.

Accordingly, an object of the present invention is to provide an oxidation catalyst which can be used to efficiently perform oxidation of a substrate (such as a hydrocarbon, an alcohol, a carbonyl compound, an ether, an amine, a sulfur compound or a heterocyclic compound) with a molecular oxygen under moderate conditions, thereby enabling economical production of a useful chemical compound with high selectivity.

Another object of the present invention is to provide a method for producing a chemical compound by using the above-mentioned oxidation catalyst.

The foregoing and other objects, features and advantages of the present invention will be apparent from the following detailed description and appended claims.

Effects of the Invention

By the use of the oxidation catalyst of the present invention, oxidation of a substrate (such as a hydrocarbon, an alcohol, a carbonyl compound, an ether, an amine, a sulfur compound or a heterocyclic compound) with a molecular oxygen can be efficiently performed under moderate conditions, thereby enabling economical production of a useful chemical compound with high selectivity.

DETAILED DESCRIPTION OF THE INVENTION

In one aspect of the present invention, there is provided an oxidation catalyst for use in the oxidation of a substrate with a molecular oxygen, comprising at least one member selected from the group consisting of a hydrazyl radical represented by the formula (1) below and a hydrazine compound represented by the formula (2) below,

[Ka 1]

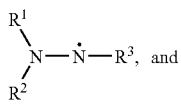
(1)

-continued

[Ka 2]

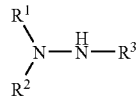
(2)

wherein each of $R^1$, $R^2$ and $R^3$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^3$ are optionally bonded to each other, to thereby form a ring.

In another aspect of the present invention, there is provided a method for producing a chemical compound, comprising contacting a substrate with a molecular oxygen in the presence of the above-mentioned oxidation catalyst, thereby performing an oxidation reaction to form a chemical compound.

For an easier understanding of the present invention, the essential features and various preferred embodiments of the present invention are enumerated below.

1. An oxidation catalyst for use in the oxidation of a substrate with a molecular oxygen, comprising at least one member selected from the group consisting of a hydrazyl radical represented by the formula (1) below and a hydrazine compound represented by the formula (2) below,

[Ka 3]

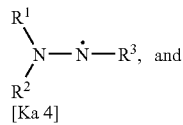
(1)

[Ka 4]

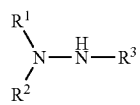
(2)

wherein each of $R^1$, $R^2$ and $R^3$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^3$ are optionally bonded to each other, to thereby form a ring.

2. The oxidation catalyst according to item 1 above, wherein the hydrazyl radical and the hydrazine compound are, respectively, represented by the following formulae (3) and (4):

[Ka 5]

(3)

[Ka 6]

(4)

wherein each of $R^4$, $R^5$, $R^6$, $R^7$ and $R^8$ independently represents a hydrogen atom, an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atoms and groups;

each of $R^1$ and $R^2$ has the same definition as each of $R^4$ to $R^8$ except that any of $R^1$ and $R^2$ does not represent a hydrogen atom; and wherein $R^1$ and $R^2$ are optionally bonded to each other, to thereby form a ring, and wherein with respect to one or two pairs of substituents selected from the group consisting of a pair of substituents $R^4$ and $R^5$, a pair of substituents $R^5$ and $R^6$, a pair of substituents $R^6$ and $R^7$ and a pair of substituents $R^7$ and $R^8$, the substituents of the or each pair are optionally bonded to each other, to thereby form a ring or two rings.

3. The oxidation catalyst according to item 1 or 2 above, wherein the hydrazyl radical is selected from the group consisting of 2,2-diphenyl-1-picrylhydrazyl, 2,2-diphenyl-1-(2, 6-dinitro-4-fluoromethylphenyl)hydrazyl, 2,2-diphenyl-1-(4-cyano-2,6-dinitrophenyl)hydrazyl, N,N-diphenyl-N'-(2, 4,6 tricyanophenyl)hydrazyl, 1,3,5-tris(N,N-diphenylhydrazyl)-2,4,6-tricyanobenzol, 2,2-di-(4-tert-octylphenyl)picrylhydrazyl, carbazol-9-yl (2,4,6-trinitrophenyl)amidogen and N-phenyl-N-(4-trifluoromethylphenyl)-N'-(2,4,6-trinitrophenyl)hydrazyl, and the hydrazine compound is selected from the group consisting of 2,2-diphenyl-1-picrylhydrazine, 2,2-diphenyl-1-(2, 6-dinitro-4-fluoromethylphenyl)hydrazine, 2,2-diphenyl-1-(4-cyano-2,6-dinitrophenyl)hydrazine, N,N-diphenyl-N'-(2, 4,6-tricyanophenyl)hydrazine, 1,3,5-tris(N,N-diphenylhydrazino)-2,4,6-tricyanobenzol, 2,2-di-(4-tert-octylphenyl)picrylhydrazine, carbazol-9-yl (2,4,6-trinitrophenyl)amine and N-phenyl-N-(4-trifluoromethylphenyl)-N'-(2,4,6-trinitrophenyl)hydrazine.

4. The oxidation catalyst according to any one of items 1 to 3 above, wherein the hydrazyl radical is 2,2-diphenyl-1-picrylhydrazyl, and the hydrazine compound is 2,2-diphenyl-1-picrylhydrazine.

5. The oxidation catalyst according to item 1 above, wherein the hydrazyl radical and the hydrazine compound are, respectively, represented by the following formulae (5) and (6):

[Ka 7]

(5)

[Ka 8]

(6)

wherein each of $R^1$, $R^2$ and $R^9$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^9$ are optionally bonded to each other, to thereby form a ring.

6. The oxidation catalyst according to item 1 or 5 above, wherein the hydrazyl radical is selected from the group consisting of 1-phenylpyrazolidone-(3)-radical and 3,4-dihydro-1,4-dioxo-3-phenyl-2-phthalazinyl, and the hydrazine compound is selected from the group consisting of 1-phenylpyrazolidine-3-one, 1-phenyl-1,2-dihydropyridazine-3,6-dione and 2-phenyl-2,3-dihydrophthalazine-1,4-dione.

7. The oxidation catalyst according to item 1 above, wherein the hydrazyl radical and the hydrazine compound are, respectively, represented by the following formulae (7) and (8):

[Ka 9]

(7)

[Ka 10]

(8)

wherein each of $R^{10}$, $R^{11}$ and $R^{12}$ independently represents a hydrogen atom, an oxygen atom, a sulfur atom, an aliphatic group, an aromatic group, a halogen atom, a hydroxyl group, a nitro group, a nitroso group, a cyano group; an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atoms and groups; $R^{13}$ has the same definition as each of $R^{10}$ to $R^{12}$ except that $R^{13}$ does not represent a hydrogen atom; and wherein two substituents selected from the group consisting of $R^{11}$, $R^{12}$ and $R^{13}$ are optionally bonded to each other, to thereby form a ring.

8. The oxidation catalyst according to item 1 or 7 above, wherein the hydrazyl radical is selected from the group consisting of 2,4,6-triphenyl-3,4-dihydro-2H-[1,2,4,5]tetrazine-1-yl, 1,3,5,6-tetraphenylverdazyl, 1,3,5-triphenyl-6-oxoverdazyl and 1,3,5-triphenyl-6-thioxoverdazyl, and the hydrazine compound is selected from the group consisting of 2,4,6-triphenyl-1,2,3,4-tetrahydro-[1,2,3,4]tetrazine, 2,3,4,6-tetraphenyl-1,2,3,4-tetrahydro-[1,2,4,5]tetrazine, 1,3,5-triphenyl-6-oxotetrazine and 1,3,5-triphenyl-6-thioxotetrazine.

9. The oxidation catalyst according to any one of items 1 to 8 above, which further comprises an oxidation promoter.

10. The oxidation catalyst according to item 9 above, wherein the oxidation promoter is a transition metal compound.

11. The oxidation catalyst according to item 10 above, wherein the transition metal is at least one member selected from the group consisting of the elements of the Groups 3 to 12 of the Periodic Table.

12. The oxidation catalyst according to item 11 above, wherein the transition metal is at least one member selected from the group consisting of lanthanoids, Ti, Zr, Hf, V, Nb, Ta, Cr, Mo, W, Mn, Re, Fe, Ru, Os, Co, Rh, Ir, Ni, Pd, Pt, Cu, Ag, Au, Zn and Cd.

13. A method for producing a chemical compound, comprising contacting a substrate with a molecular oxygen in the presence of the oxidation catalyst of any one of items 1 to 12 above, thereby performing an oxidation reaction to form a chemical compound.

14. The method according to item 13 above, wherein the substrate is selected from the group consisting of a hydrocarbon, an alcohol, a carbonyl compound, an ether, an amine, a sulfur compound and a heterocyclic compound.

15. The method according to item 14 above, wherein the amine is a primary amine, and the chemical compound produced is an oxime compound or a nitro compound.

16. The method according to item 15 above, wherein the primary amine is represented by the following formula (9):

[Ka 11]

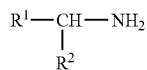

(9)

wherein each of $R^1$ and $R^2$ independently represents a hydrogen atom, an aliphatic group, an aromatic group or an aralkyl group, provided that $R^1$ and $R^2$ are not simultaneously hydrogen atoms; and wherein $R^1$ and $R^2$ are optionally bonded to each other, to thereby form a ring.

17. The method according to item 16 above, wherein the primary amine is cyclohexylamine, and the chemical compound produced is cyclohexanone oxime.

18. The method according to item 14 above, wherein the amine is a secondary amine, and the chemical compound produced is a nitrone compound.

19. The method according to item 18 above, wherein the secondary amine is represented by the following formula (10):

[Ka 12]

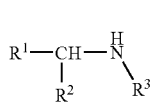

(10)

wherein each of $R^1$ and $R^2$ independently represents a hydrogen atom, an aliphatic group, an aromatic group or an aralkyl group, and $R^3$ has the same definition as each of $R^1$ and $R^2$ except that $R^3$ does not represent a hydrogen atom; and wherein two substituents selected from the group consisting of $R^1$, $R^2$ and $R^3$ are optionally bonded to each other, to thereby form a ring.

20. The method according to any one of items 13 to 19 above, wherein the oxidation reaction is either performed in a reaction medium which is at least one member selected from the group consisting of water and an organic solvent, or performed using the substrate as a reaction medium.

21. The method according to item 20 above, wherein the organic solvent is an aprotic solvent.

22. The method according to item 21 above, wherein the aprotic solvent is at least one member selected from the group consisting of a nitrile, a nitro compound, an ester, an ether and an amide.

23. The method according to item 22 above, wherein the nitrile is at least one member selected from the group consisting of acetonitrile and benzonitrile.

24. The method according to item 22 above, wherein the amide is at least one member selected from the group consisting of dimethylformamide and dimethylacetamide.

25. The method according to any one of items 13 to 24 above, wherein the at least one compound selected from the group consisting of the hydrazyl radical and the hydrazine compound is used in an amount of from 0.0001 to 1 mole per mole of the substrate.

26. The method according to any one of items 13 to 25 above, wherein the oxidation catalyst further comprises an oxidation promoter, and the oxidation promoter is used in an amount of from 0.00005 to 0.8 mole per mole of the substrate.

27. The method according to any one of items 13 to 26 above, wherein the oxidation reaction is performed under reaction conditions wherein the temperature is from 0 to 200° C. and the pressure is from atmospheric pressure to 20 MPa.

Hereinbelow, the present invention is described in detail.

The oxidation catalyst of the present invention is an oxidation catalyst for use in the oxidation of a substrate with a molecular oxygen, comprising at least one member selected from the group consisting of a hydrazyl radical represented by the formula (1) below and a hydrazine compound represented by the formula (2) below,

[Ka 13]

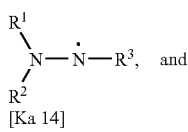

(1)

and

[Ka 14]

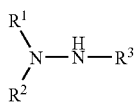

(2)

wherein each of $R^1$, $R^2$ and $R^3$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^3$ are optionally bonded to each other, to thereby form a ring.

The aliphatic group mentioned above may be unsaturated or saturated, may be unsubstituted or substituted with a substituent, and may be linear, cyclic or branched. Further, the aliphatic group may contain one or more members selected from the group consisting of an oxygen atom, a nitrogen atom, a sulfur atom, a silicon atom, a phosphorus atom, a boron atom and a halogen atom. The aromatic group mentioned above may be unsubstituted or substituted with a substituent, and may contain one or more members selected from the group consisting of an oxygen atom, a nitrogen atom, a sulfur atom, a silicon atom, a phosphorus atom, a boron atom and a halogen atom. The hydroxyl group mentioned above may form a salt with a metal atom. A nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group. In general, the aliphatic group has 1 to 15 carbon atoms, preferably 1 to 10 carbon atoms; the aromatic group has 5 to 12 carbon atoms, preferably 6 to 10 carbon atoms; the acyl group has 1 to 10 carbon atoms, preferably 1 to 6 carbon atoms; the alkoxycarbonyl group has 1 to 10 carbon atoms, preferably 1 to 6 carbon atoms; the aryloxycarbonyl group has 5 to 10 carbon atoms; the alkoxyl group has 1 to 10 carbon atoms, preferably 1 to 6 carbon atoms; the aryloxy group has 5 to 10 carbon atoms; the haloalkyl group has 1 to 6 carbon atoms; and the alkylthio group has 1 to 6 carbon atoms. In the present invention, the term "heterocyclic group" means a substituent formed from a heteromonocyclic compound, such as furan, thiophene, pyrrole, γ-pyran, thiopyran, pyridine, morpholine, thiazole, imidazole, pyrimidine and 1,3,5-triazine; or a condensed heterocyclic compound, such as indole, quinoline, purine, pteridine, chromane, carbazole, benzothiazole, benzotriazole, benzoisoquinoline and thienopyridine.

Preferred examples of $R^1$ and $R^2$ in the formulae (1) and (2) above include an aliphatic group, an aromatic group, a carbonyl group, a carboxyl group, an acyl group, an alkoxycarbonyl group, an aryloxycarbonyl group, a haloalkyl group and a heterocyclic group. Preferred examples of $R^3$ include an aliphatic group, an aromatic group, a cyano group, a carbonyl group, a carboxyl group, an acyl group, an alkoxycarbonyl group, an aryloxycarbonyl group, a carbamoyl group, a haloalkyl group and a heterocyclic group. These groups may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group.

As preferred examples of hydrazyl radicals represented by the formula (1) above and a hydrazine compound represented by the formula (2) above, there can be mentioned a hydrazyl radical and a hydrazine compound respectively represented by the following formulae (3) and (4):

[Ka 15]

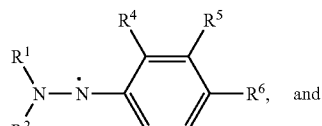

(3)

and

[Ka 16]

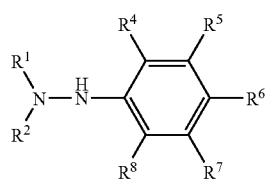

(4)

wherein each of $R^4$, $R^5$, $R^6$, $R^7$ and $R^8$ independently represents a hydrogen atom, an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atoms and groups;

each of $R^1$ and $R^2$ has the same definition as each of $R^4$ to $R^8$ except that any of $R^1$ and $R^2$ does not represent a hydrogen atom; and wherein $R^1$ and $R^2$ are optionally bonded to each other, to thereby form a ring, and wherein with respect to one or two pairs of substituents selected from the group consisting of a pair of substituents $R^4$ and $R^5$, a pair of substituents $R^5$ and $R^6$, a pair of substituents $R^6$ and $R^7$ and a pair of substituents $R^7$ and $R^8$, the substituents of the or each pair are optionally bonded to each other, to thereby form a ring or two rings.

The aliphatic group mentioned above may be unsaturated or saturated, may be unsubstituted or substituted with a substituent, and may be linear, cyclic or branched. Further, the aliphatic group may contain one or more members selected from the group consisting of an oxygen atom, a nitrogen atom, a sulfur atom, a silicon atom, a phosphorus atom, a boron atom and a halogen atom. The aromatic group mentioned above may be unsubstituted or substituted with a substituent, and may contain one or more members selected from the group consisting of an oxygen atom, a nitrogen atom, a sulfur atom, a silicon atom, a phosphorus atom, a boron atom and a halogen atom. The hydroxyl group mentioned above may form a salt with a metal atom.

A nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group. With respect to the number of carbon atoms of each substituent above, the same explanation as made above in connection with the formulae (1) and (2) applies here.

Preferred examples of $R^1$ and $R^2$ in the formulae (3) and (4) include an aliphatic group, an aromatic group, a carbonyl group, a carboxyl group, an acyl group, an alkoxycarbonyl group, an aryloxycarbonyl group, a haloalkyl group and a heterocyclic group. Further, preferred examples of $R^4$, $R^5$, $R^6$, $R^7$ and $R^8$ include a hydrogen atom, an aliphatic group, an aromatic group, a halogen atom, a nitro group, a cyano group, an amino group, an imino group, a carbonyl group, a carboxyl group, an acyl group, an alkoxycarbonyl group, an aryloxycarbonyl group, a carbamoyl group, an alkoxyl group, an aryloxy group, a haloalkyl group, a sulfo group, a sulfinyl group, a sulfonyl group and a heterocyclic group.

These groups may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group.

Specific examples of hydrazyl radicals represented by the formula (3) above include triphenylhydrazyl, 2,2-diphenyl-1-(5'-phenyl-m-terphenyl-2'-yl)hydrazyl, 2,2-diphenyl-(2-nitrophenyl)hydrazyl, 2,2-diphenyl-(2,4-dinitrophenyl)hydrazyl, 2,2-diphenyl-1-picrylhydrazyl, 2,2-diphenyl-1-(3-chloro-2,4,6-trinitrophenyl)hydrazyl, 1-[3-(4-morpholinyl)-2,4,6-trinitrophenyl]-2,2-diphenylhydrazyl, 2,2-diphenyl-1-(2,6-dinitro-4-fluoromethylphenyl)hydrazyl, N'-(2,4-dinitro-6-trifluoromethylphenyl)-N,N-diphenylhydrazyl, 2,2-diphenyl-1-(4-cyano-2,6-dinitrophenyl)hydrazyl, 4-(N',N'-diphenylhydrazyl)3,5-dinitrobenzoyl chloride, N,N-diphenyl-N'-(2,6-dinitro-4-carboxyphenyl)hydrazyl, 2,2-diphenyl-1-(2,6-dinitro-4-methoxycarbonyl-phenyl) hydrazyl, N,N-diphenyl-N'-(2,6-dinitro-4-sulfophenyl) hydrazyl, N,N-diphenyl-N'-(2,4-dinitro-6-sulfophenyl) hydrazyl, N-cyclohexyl-4-(N',N'-diphenylhydrazyl)-3,5-dinitrobenzamide, N,N-diphenyl-N'-(2,4,6-tricyanophenyl) hydrazyl, N,N-diphenyl-N'-(3,5-dichloro-2,4,6-tricyanophenyl)hydrazyl, 2,2-diphenyl-1-(2,4,6-tricyano-3,5-difluorophenyl)hydrazyl, 2,2-diphenyl-1-[2,4,6-tris-(methoxycarbonyl)-phenyl]hydrazyl, 2,2-diphenyl-1-(2,4,6-tris(trifluoromethylsulfonyl)phenyl)hydrazyl, N,N-diphenyl-3,5-dichloro-2,4,6-tricyanophenolhydrazyl, 1,3-bis-(N,N-diphenylhydrazyl)-5-chloro-2,4,6-tricyanobenzol, 1,3,5-tris(N,N-diphenylhydrazyl)-2,4,6-tricyanobenzol, 1,3,5-tris(N,N-diphenylhydrazyl)-2,4,6-trinitrobenzol, 2,2-di-(4-tert-octylphenyl)picrylhydrazyl, 1-picryl-2,2-di-(biphenylyl-(4))hydrazyl, 2,2-di-2-naphthyl-1-picrylhydrazyl, 1-(1)naphthyl-1-phenyl-1-picrylhydrazyl, carbazol-9-yl (2,4,6-trinitrophenyl) amidogen, 2-(4-fluorophenyl)-2-phenyl-1-(2,4,6-trinitrophenyl)hydrazyl, N-phenyl-N-(4-trifluoromethylphenyl)-N'-(2,4,6-trinitrophenyl)hydrazyl, (3-chloro-carbazol-9-yl)-(2,4,6-trinitrophenyl)amidogen, 9-amino-N-picryl-3,6-dibromocarbazyl, 1-picryl-2,2-bis-(4-methoxycarbonyl-phenyl)hydrazyl, p,p'-disulfo-1,1-diphenyl-2-picrylhydrazyl, N'-phenyl-N'-thiazole-2-yl-N-(2,4,6-trinitrophenyl)hydrazyl, N'-benzothiazole-2-yl-N'-phenyl-N-(2,4,6-trinitrophenyl)hydrazyl, N'-benzoxazole-2-yl-N'-phenyl-N-(2,4,6-trinitrophenyl)hydrazyl, carbazol-9-yl (2,6-dinitrophenyl) amidogen, N-carbazoyl-N-2,4,6-trinitro-5-chlorophenylaminyl radical, 9-amino-N-(3-cyano-2,4,6-trinitrophenyl)carbazyl, N-carbazol-9-yl-2,4,6-trinitro-3-piperidino-anilino, carbazol-9-yl-(3-morpholine-4-yl-2,4,6-trinitrophenyl)-aminyl and N'-benzoxazole-2-yl-N'-phenyl-N-(2,4-trinitrophenyl)hydrazyl.

Preferred examples of hydrazyl radicals represented by the formula (3) include 2,2-diphenyl-1-picrylhydrazyl, 2,2-diphenyl-1-(2,6-dinitro-4-fluoromethylphenyl)hydrazyl, 2,2-diphenyl-1-(4-cyano-2,6-dinitrophenyl)hydrazyl, 2,2-diphenyl-1-(2,6-dinitro-4-methoxycarbonyl-phenyl)hydrazyl, N,N-diphenyl-N'-(2,6-dinitro-4-sulfophenyl)hydrazyl, N,N-diphenyl-N-(2,4,6-tricyanophenyl)hydrazyl, 2,2-diphenyl-1-(2,4,6-tricyano-3,5-difluorophenyl)hydrazyl, 1,3,5-tris(N,N-diphenylhydrazyl)-2,4,6-tricyanobenzol, 1,3,5-tris(N, N-diphenylhydrazyl)-2,4,6-trinitrobenzol, 2,2-di-(4-tert-octylphenyl)picrylhydrazyl, carbazol-9-yl(2,4,6-trinitrophenyl) amidogen, N-phenyl-N-(4-trifluoromethylphenyl)-N'-(2,4,6-trinitrophenyl)hydrazyl, 1-picryl-2,2-bis-(4-methoxycarbonyl-phenyl)hydrazyl, p,p'-disulfo-1,1-diphenyl-2-picrylhydrazyl and 9-amino-N-(3-cyano-2,4,6-trinitrophenyl)carbazyl. Among the above-mentioned hydrazyl radicals, more preferred are 2,2-diphenyl-1-picrylhydrazyl, 2,2-diphenyl-1-(2,6-dinitro-4-fluoromethylphenyl)hydrazyl, 2,2-diphenyl-1-(4-cyano-2,6-dinitrophenyl)hydrazyl, N,N-diphenyl-N'-(2,4,6-tricyanophenyl)hydrazyl, 1,3,5-tris(N,N-diphenylhydrazyl)-2,4,6-tricyanobenzol, 2,2-di-(4-tert-octylphenyl)picrylhydrazyl, carbazol-9-yl (2,4,6-trinitrophenyl) amidogen, N-phenyl-N-(4-trifluoromethylphenyl)-N'-(2,4,6-trinitrophenyl)hydrazyl and the like, and especially preferred is 2,2-diphenyl-1-picrylhydrazyl.

Specific examples of hydrazine compounds represented by the formula (4) above include triphenylhydrazine, 2,2-diphenyl-1-(5'-phenyl-m-terphenyl-2'-yl)hydrazine, 2,2-diphenyl-(2-nitrophenyl)hydrazine, 2,2-diphenyl-(2,4-dinitrophenyl)hydrazine, 2,2-diphenyl-1-picrylhydrazine, 2,2-diphenyl-1-(3-chloro-2,4,6-trinitrophenyl)hydrazine, 1-[3-(4-morpholinyl)-2,4,6-trinitrophenyl]-2,2-diphenylhydrazine, 2,2-diphenyl-1-(2,6-dinitro-4-fluoromethylphenyl)hydrazine, N'-(2,4-dinitro-6-trifluoromethylphenyl)-N,N-diphenylhydrazine, 2,2-diphenyl-1-(4-cyano-2,6-dinitrophenyl)hydrazine, 4-(N',N'-diphenylhydrazino) 3,5-dinitrobenzoyl chloride, N,N-diphenyl-N'-(2,6-dinitro-4-carboxyphenyl)hydrazine, 2,2-diphenyl-1-(2,6-dinitro-4-methoxycarbonyl-phenyl)hydrazine, N,N-diphenyl-N'-(2,6-dinitro-4-sulfophenyl)hydrazine, 2,2-diphenyl-1-(2,4-dinitro-6-sulfophenyl)hydrazine, N-cyclohexyl-4-(N',N'-diphenylhydrazino)-3,5-dinitrobenzamide, N,N-diphenyl-N-(2,4,6-tricyanophenyl)hydrazine, N,N-diphenyl-N'-(3,5-dichloro-2,4,6-tricyanophenyl)hydrazine, 2,2-diphenyl-1-(2,4,6-tricyano-3,5-difluorophenyl)hydrazine, 2,2-diphenyl-1-[2,4,6-tris-(methoxycarbonyl)-phenyl]hydrazine, 2,2-diphenyl-1-(2,4,6-tris(trifluoromethylsulfonyl)phenyl)hydrazine, 2,4-dichloro-6-(N,N'-diphenylhydrazino)-benzene-1,3,5-tricarbonitrile, tricyano-monochloro-bis-(diphenylhydrazino)benzol, 1,3,5-tris(N,N-diphenylhydrazino)-2,4,6-tricyanobenzol, 1,3,5-tris(N,N-diphenylhydrazino)-2,4,6-trinitrobenzol, 2,2-di-(4-tert-octylphenyl)picrylhydrazine, 1-picryl-2,2-di-(biphenyl)-1-(4))hydrazine, 2,2-di-2-naphthyl-1-picrylhydrazine, 1-(1)naphthyl-1-phenyl-1-picrylhydrazine, carbazol-9-yl (2,4,6-trinitrophenyl)amine, 2-(4-fluorophenyl)-2-phenyl-1-(2,4,6-trinitrophenyl)hydrazine, N-phenyl-N-(4-trifluoromethylphenyl)-N'-(2,4,6-trinitrophenyl)hydrazine, (3-chloro-carbazol-9-yl)-(2,4,6-trinitrophenyl)amine, (3,6-dibromocarbazol-9-yl)-(2,4,6-trinitrophenyl)amine, 1-picryl-2,2-bis-(4-methoxycarbonyl-phenyl)hydrazine, p,p'-disulfo-1,1-diphenyl-2-picrylhydrazine, N'-phenyl-N'-thiazole-2-yl-N-(2,4,6-trinitrophenyl)hydrazine, N'-benzothiazole-2-yl-N'-phenyl-N-(2,4,6-trinitrophenyl)hydrazine, N'-benzoxazole-2-yl-N'-phenyl-N-(2,4,6-trinitrophenyl)hydrazine, carbazol-9-yl (2,6-dinitrophenyl)amine, carbazol-9-yl(3-chloro-2,4,6-trinitrophenyl)amine, 3-(carbazol-9-yl-amino)-2,4,6-trinitro-benzonitrile, carbazol-9-yl-(2,4,6-trinitro-3-piperidine-1-yl-phenyl)amine, carbazol-9-yl-(3-morpholine-4-yl-2,4,6-trinitrophenyl)amine and 2-(2,4,6-trinitro-anilino)-isoindoline-1,3-dione.

Preferred examples of hydrazine compounds represented by the formula (4) include 2,2-diphenyl-1-picrylhydrazine, 2,2-diphenyl-1-(2,6-dinitro-4-fluoromethylphenyl)hydrazine, 2,2-diphenyl-1-(4-cyano-2,6-dinitrophenyl)hydrazine, 2,2-diphenyl-1-(2,6-dinitro-4-methoxycarbonyl-phenyl)hydrazine, 2,2-diphenyl-1-(2,6-dinitro-4-sulfophenyl)hydrazine, N,N-diphenyl-N'-(2,4,6-tricyanophenyl)hydrazine, N,N-diphenyl-N'-(2,4,6-tricyano-3,5-difluorophenyl)hydrazine, 1,3,5-tris(N,N-diphenylhydrazino)-2,4,6-tricyanobenzol, 1,3,5-tris(N,N-diphenylhydrazino)-2,4,6-trinitrobenzol, 2,2-di-(4-tert-octylphenyl)picrylhydrazine, carbazol-9-yl (2,4,6-trinitrophenyl)amine, N-phenyl-N-(4-trifluoromethylphenyl)-N'-(2,4,6-trinitrophenyl)hydrazine, 1-picryl-2,2-bis-(4-methoxycarbonyl-phenyl)hydrazine, p,p'-disulfo-1,1-diphenyl-2-picrylhydrazine and 3-(carbazol-9-yl-amino)-2,4,6-trinitro-benzonitrile. Among the above-mentioned hydrazine compounds, more preferred are 2,2-diphenyl-1-picrylhydrazine, 2,2-diphenyl-1-(2,6-dinitro-4-fluoromethylphenyl)hydrazine, 2,2-diphenyl-1-(4-cyano-2,6-dinitrophenyl)hydrazine, N,N-diphenyl-N'-(2,4,6-tricyanophenyl)hydrazine, 1,3,5-tris(N,N-diphenylhydrazino)-2,4,6-tricyanobenzol, 2,2-di-(4-tert-octylphenyl)picrylhydrazine, carbazol-9-yl (2,4,6-trinitrophenyl)amine, N-phenyl-N-(4-trifluoromethylphenyl)-N'-(2,4,6-trinitrophenyl)hydrazine and the like, and especially preferred is 2,2-diphenyl-1-picrylhydrazine.

Further, as preferred examples of hydrazyl radicals represented by the formula (1) and a hydrazine compound represented by formula (2), there can be mentioned a hydrazyl radical and a hydrazine compound respectively represented by the following formulae (5) and (6):

[Ka 17]

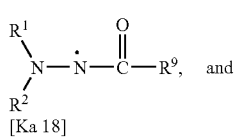

(5)

and

[Ka 18]

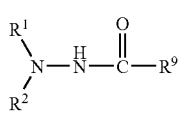

(6)

wherein each of $R^1$, $R^2$ and $R^9$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^9$ are optionally bonded to each other, to thereby form a ring.

The aliphatic group mentioned above may be unsaturated or saturated, may be unsubstituted or substituted with a substituent, and may be linear, cyclic or branched. Further, the aliphatic group may contain one or more members selected from the group consisting of an oxygen atom, a nitrogen atom, a sulfur atom, a silicon atom, a phosphorus atom, a boron atom and a halogen atom. The aromatic group mentioned above may be unsubstituted or substituted with a substituent, and may contain one or more members selected from the group consisting of an oxygen atom, a nitrogen atom, a sulfur atom, a silicon atom, a phosphorus atom, a boron atom and a halogen atom. The hydroxyl group mentioned above may form a salt with a metal atom. A nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group. With respect to the number of carbon atoms of each substituent above, the same explanation as made above in connection with the formulae (1) and (2) applies here.

Preferred examples of $R^1$ and $R^2$ in the formulae (5) and (6) above include an aliphatic group, an aromatic group, a carbonyl group, a carboxyl group, an acyl group, an alkoxycarbonyl group, an aryloxycarbonyl group, a haloalkyl group and a heterocyclic group. Preferred examples of $R^9$ include an aliphatic group, an aromatic group, an alkoxyl group, an aryloxy group, a haloalkyl group and a heterocyclic group. These groups may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group.

Specific examples of hydrazyl radicals represented by the formula (5) above include N-benzoyl-N,N'-diphenylhydrazyl, 1-(3,5-dinitrobenzoyl)-2,2-diphenylhydrazyl, N-(2-nitrobenzoyl)-N',N'-diphenylhydrazyl, N-benzoyl-N',N'-bis-(4-nitrophenyl)hydrazine, 1-(trifluoroacetyl)-2,2-bis(3,5-di-tert-butylphenyl)hydrazyl, tribenzoylhydrazoyl radical, 1-phenylpyrazolidone-(3)-radical, 5-methyl-1-phenyl-3-pyrazolidone radical, 2,5-dioxo-4-phenyl-[1,3,4]oxadiazolidine-3-yl, 4,4-dimethyl-3,5-dioxo-2-phenyl-1-pyrazolidinyl, 1-phenyl-4,4-diethylpyrazolidine-3,5-dione-radical, 3,4-dihydro-1,4-dioxo-3-phenyl-2-phthalazinyl, 3,4-dihydro-3-(4-nitrophenyl)-1,4-dioxo-2-phthalazinyl, 1-tert-butyl-4-methylurazole-radical, 4-(1,1-dimethylethyl)3,5-dioxo-2-phenyl-1,2,4-triazolidine, 1-α-cumyl-4-tert-butylurazole-radical, 1-tert-butyl-4-phenylurazole-radical and 3,5-dioxo-2,4-diphenyl-1,2,4-triazolidine.

Preferred examples of hydrazyl radicals represented by the formula (5) above include 1-(3,5-dinitrobenzoyl)-2,2-diphenylhydrazyl, tribenzoylhydrazoyl radical, 1-phenylpyrazolidone-(3)-radical, 2,5-dioxo-4-phenyl-[1,3,4]oxadiazolidine-3-yl, 3,4-dihydro-1,4-dioxo-3-phenyl-2-phthalazinyl and 3,4-dihydro-3-(4-nitrophenyl)-1,4-dioxo-2-phthalazinyl.

Among the above-mentioned hydrazyl compounds, more preferred are 1-phenylpyrazolidone-(3)-radical, 3,4-dihydro-1,4-dioxo-3-phenyl-2-phthalazinyl and the like.

Specific examples of hydrazine compounds represented by the formula (6) above include benzoic acid-(N',N'-diphenylhydrazide), 1-(3,5-dinitrobenzoyl)-2,2-diphenylhydrazine, 2-nitro-benzoic acid-(N',N'-diphenylhydrazide), benzoic acid-[N',N'-bis-(4-nitrophenyl)hydrazide], 1-(trifluoroacetyl)-2,2-bis(3,5-di-tert-butylphenyl)hydrazide, tribenzoylhydrazine, 1-phenylpyrazolidine-3-one, 5-methyl-1-phenyl-3-pyrazolidine-3-one, 3-phenyl-[1,3,4]oxadiazolidine-2,5-dione, 4,4-dimethyl-1-phenylpyrazolidine-3,5-dione, 4,4-diethyl-1-phenylpyrazolidine-3,5-dione, 1-phenyl-1,2-dihydropyridazine-3,6-dione, 2-phenyl-2,3-dihydrophthalazine-1,4-dione, 2-(4-nitrophenyl)-2,3-dihydrophthalazine-1,4-dione, 1-tert-butyl-4-methyl-[1,2,4]triazolidine-3,5-dione, 4-methyl-1-phenyl-[1,2,4]triazolidine-3,5-dione, 4-tert-butyl-1-(1-methyl-1-phenylethyl)-[1,2,4]triazolidine-3,5-dione, 1-tert-butyl-4-phenyl-[1,2,4]triazolidine-3,5-dione, and 1,4-diphenyl-[1,2,4]triazolidine-3,5-dione.

Preferred examples of hydrazine compounds represented by the formula (6) above include 1-(3,5-dinitrobenzoyl)-2,2-diphenylhydrazine, tribenzoylhydrazine, 1-phenylpyrazolidine-3-one, 3-phenyl-[1,3,4]oxadiazolidine-2,5-dione, 1-phenyl-1,2-dihydropyridazine-3,6-dione, 2-phenyl-2,3-dihydrophthalazine-1,4-dione and 2-(4-nitrophenyl)-2,3-dihydrophthalazine-1,4-dione. Among the above-mentioned hydrazine compounds, more preferred are 1-phenylpyrazolidine-3-one, 1-phenyl-1,2-dihydropyridazine-3,6-dione, 2-phenyl-2,3-dihydrophthalazine-1,4-dione and the like.

Further, as other preferred examples of hydrazyl radicals represented by the formula (1) and a hydrazine compound represented by the formula (2), there can be mentioned hydrazyl radical and hydrazine compound respectively represented by the following formulae (7) and (8):

[Ka 19]

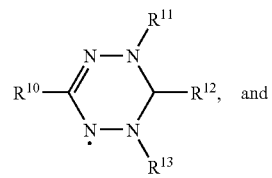

(7)

[Ka 20]

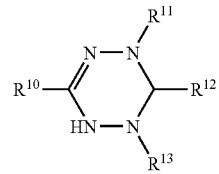

(8)

wherein each of $R^{10}$, $R^{11}$ and $R^{12}$ independently represents a hydrogen atom, an oxygen atom, a sulfur atom, an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atoms and groups;
$R^{13}$ has the same definition as each of $R^{10}$ to $R^{12}$ except that $R^{13}$ does not represent a hydrogen atom; and wherein two substituents selected from the group consisting of $R^{11}$, $R^{12}$ and $R^{13}$ are optionally bonded to each other, to thereby form a ring.

The aliphatic group may be unsaturated or saturated, may be unsubstituted or substituted with a substituent, and may be linear, cyclic or branched. Further, the aliphatic group may contain one or more members selected from the group consisting of an oxygen atom, a nitrogen atom, a sulfur atom, a silicon atom, a phosphorus atom, a boron atom and a halogen atom. The aromatic group may be unsubstituted or substituted with a substituent, and may contain one or more members selected from the group consisting of an oxygen atom, a nitrogen atom, a sulfur atom, a silicon atom, a phosphorus atom, a boron atom and a halogen atom. The hydroxyl group may form a salt with a metal atom. A nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group may also be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned group are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group. With respect to the number of carbon atoms of each substituent above, the same explanation as made above in connection with the formulae (1) and (2) applies here.

Preferred examples of $R^{10}$, $R^{11}$ and $R^{12}$ in the formulae (7) and (8) above include a hydrogen atom, an oxygen atom, a sulfur atom, an aliphatic group, an aromatic group, a nitro group, an amino group, an imino group, a carbonyl group, an acyl group, an alkoxycarbonyl group, an aryloxycarbonyl group, an alkoxyl group, an aryloxy group, and a heterocyclic group. Further, preferred examples of $R^{13}$ are the same as those (except a hydrogen atom) exemplified in connection with $R^{10}$, $R^{12}$ and $R^{13}$. These groups may be unsubstituted or substituted with a substituent, and may contain one or more members selected from the group consisting of an oxygen atom, a nitrogen atom, a sulfur atom, a silicon atom, a phosphorus atom, a boron atom and a halogen atom. When the above-mentioned groups are substituted with a substituent, examples of substituents include an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group and a heterocyclic group.

Specific examples of hydrazyl radicals represented by the formula (7) include 2,4,6-triphenyl-3,4-dihydro-2H-[1,2,4,5]tetrazine-1-yl, 1,3,5-tris-(p-chlorophenyl)verdazyl, 2,6-diphenyl-4-pentafluorophenylverdazyl, 2,4-bisperfluorophenyl-6-phenylverdazyl, 2,4,6-trisperfluorophenylverdazyl, 2-(2,3,4,5,6-pentafluorophenyl)-4,6-diphenyl-1,2,3,4-tetrahydro-[1,2,4,5]verdazyl, 2,4,6-triphenyl-1,2,3,4-tetrahydro-[1,2,4,5]verdazyl, 1-(4-nitrophenyl)-3,5-diphenylverdazyl, 6-anthracene-9-yl-2,4-diphenyl1,2,3,4-tetrahydro-[1,2,4,5]verdazyl, 3-nitro-1,5-diphenylverdazyl, 3-(3-pyridyl)-1,5-diphenylverdazyl, 2-benzothiazole-2-yl-4,6-diphenyl-3,4-dihydro-2H-[1,2,4,5]tetrazine-1-yl, 1,3,5,6-tetraphenylverdazyl, 3-(4-nitrophenyl)-1,5,6-triphenylverdazyl, 6-methyl-3-nitro-1,5-diphenylverdazyl, 1,5-dimethyl-3-phenyl-6-oxoverdazyl, 1,5-dimethyl-3-(2-pyridyl)-6-oxoverdazyl, 1,3,5-triphenyl-6-oxoverdazyl, 1,3,5-trimethyl-6-thioxoverdazyl, 1,3,5-triphenyl-6-thioxoverdazyl and 3-(4-nitrophenyl)-1,5-diphenyl-6-thioxoverdazyl.

Preferred examples of hydrazyl radicals represented by the formula (7) include 2,4,6-triphenyl-3,4-dihydro-2H-[1,2,4,5]tetrazine-1-yl, 2-(2,3,4,5,6-pentafluorophenyl)-4,6-diphenyl-1,2,3,4-tetrahydro-[1,2,3,4]verdazyl, 1-(4-nitrophenyl)-3,5-diphenylverdazyl, 6-anthracene-9-yl-2,4-diphenyl1,2,3,4-tetrahydro-[1,2,4,5]verdazyl, 1,3,5,6-tetraphenylverdazyl, 6-methyl-3-nitro-1,5-diphenylverdazyl, 1,3,5-triphenyl-6-oxoverdazyl and 1,3,5-triphenyl-6-thioxoverdazyl. Among the above-mentioned hydrazyl radicals, more preferred are 2,4,6-triphenyl-3,4-dihydro-2H-[1,2,4,5]tetrazine-1-yl, 1,3,5,6-tetraphenylverdazyl, 1,3,5-triphenyl-6-oxoverdazyl, 1,3,5-triphenyl-6-thioxoverdazyl and the like.

Specific examples of hydrazine compounds represented by the formula (8) include 2,4,6-triphenyl-1,2,3,4-tetrahydro-[1,2,3,4]tetrazine, 1,3,5-tris-(p-chlorophenyl)tetrazine, 2,6-diphenyl-4-pentafluoro-1,2,3,4-tetrahydro-tetrazine, 2,4-bis(perfluorophenyl)-6-phenyl-1,2,3,4-tetrahydro-tetrazine, 2,4,6-tris(perfluorophenyl)-1,2,3,4-tetrahydro-tetrazine, 2-(2,3,4,5,6-pentafluorophenyl)-4,6-diphenyl-1,2,3,4-tetrahydro-[1,2,4,5]tetrazine, 2,4,6-triphenyl-1,2,3,4-tetrahydro-[1,2,4,5]tetrazine, 2-(4-nitrophenyl)-4,6-diphenyl-1,2,3,4-tetrahydro-[1,2,4,5]tetrazine, 6-anthracene-9-yl-2,4-diphenyl1,2,3,4-tetrahydro-[1,2,4,5]tetrazine, 6-nitro-2,4-diphenyl-1,2,3,4-tetrahydro-[1,2,4,5]tetrazine, 3-(3-pyridyl)-1,5-diphenyltetrazine, 2-benzothiazole-2-yl-4,6-diphenyl-1(6), 2,3,4-tetrahydro-[1,2,4,5]tetrazine, 2,3,4,6-tetraphenyl-1,2,3,4-tetrahydro-[1,2,4,5]tetrazine, 3-(4-nitrophenyl)-1,5,6-triphenyltetrazine, 3-methyl-6-nitro-2,4-diphenyl-1,2,3,4-tetrahydro-[1,2,4,5]tetrazine, 1,4-dihydro-2,4-dimethyl-6-phenyl-1,2,4,5-tetrazine-3(2H)-one, 2,4-dimethyl-6-pyridine-2-yl-1,4-dihydro-2H-[1,2,4,5]tetrazine-3-one, 1,3,5-triphenyl-6-oxotetrazine, 1,3,5-trimethyl-6-thioxotetrazine, 1,3,5-triphenyl-6-thioxotetrazine and 3-(4-nitrophenyl)-1,5-diphenyl-6-thioxotetrazine.

Preferred examples of hydrazine compounds represented by the formula (8) include 2,4,6-triphenyl-1,2,3,4-tetrahydro-[1,2,3,4]tetrazine, 2-(2,3,4,5,6-pentafluorophenyl)-4,6-diphenyl-1,2,3,4-tetrahydro-[1,2,4,5]tetrazine, 2,4,6-triphenyl-1,2,3,4-tetrahydro-[1,2,4,5]tetrazine, 2-(4-nitrophenyl)-4,6-diphenyl-1,2,3,4-tetrahydro-[1,2,4,5]tetrazine, 6-anthracene-9-yl-2,4-diphenyl1,2,3,4-tetrahydro-[1,2,4,5]tetrazine, 2,3,4,6-tetraphenyl-1,2,3,4-tetrahydro-[1,2,4,5]tetrazine, 3-methyl-6-nitro-2,4-diphenyl-1,2,3,4-tetrahydro-[1,2,4,5]tetrazine, 1,3,5-triphenyl-6-oxotetrazine and 1,3,5-triphenyl-6-thioxotetrazine. Among the above-mentioned hydrazine compounds, more preferred are 2,4,6-triphenyl-1,2,3,4-tetrahydro-[1,2,3,4]tetrazine, 2,3,4,6-tetraphenyl-1,2,3,4-tetrahydro-[1,2,4,5]tetrazine, 1,3,5-triphenyl-6-oxotetrazine, 1,3,5-triphenyl-6-thioxotetrazine and the like.

These compounds (at least one member selected from the group consisting of a hydrazyl radical represented by the formula (1) and a hydrazine compound represented by the formula (2)) may be used individually or in combination (hereinafter, the above-mentioned at least one member is frequently referred to as "hydrazyl radical of formula (1) and/or hydrazine compound of formula (2)"). Further, the amount of hydrazyl radical of formula (1) and/or hydrazine compound of formula (2) may vary depending on the type of the oxidation reaction, and there is no particular limitation as long as the desired catalytic effect can be achieved. However, the amount is generally from 0.0001 to 1 mole, preferably from 0.0005 to 0.5 mole, more preferably 0.001 to 0.3 mole, per mole of the substrate.

When the above-mentioned compounds (i.e., hydrazyl radical of formula (1) and hydrazine compound of formula (2)) are used in combination as a mixture, the amount of each compound is generally from 0.001 to 0.999 mole, preferably from 0.01 to 0.99 mol, more preferably 0.1 to 0.9 mole per mole of the other compound.

The at least one member selected from the group consisting of a hydrazyl radical represented by the formula (1) and a hydrazine compound represented by the formula (2) may be carried on a carrier. Examples of carriers include an organic polymer or a porous inorganic carrier, such as silica, silica-alumina, zeolite and activated carbon. Further, the hydrazyl radical of formula (1) and/or hydrazine compound of formula (2) may be used in the form a complex with an oxidation promoter (such as a transition metal compound which is explained below), wherein, in the complex, the oxidation promoter serves as a carrier for the hydrazyl radical of formula (1) and/or hydrazine compound of formula (2).

A hydrazyl radical represented by the formula (1) and a hydrazine compound represented by the formula (2) can be prepared by conventional reaction methods. For example, a hydrazine compound represented by the formula (2) is prepared as follows: a hydrazine compound having substituents which are the same as $R^1$ and $R^2$ in the formula (2) and a halide having a substituent which is the same as $R^3$ in the formula (2) are subjected to condensation reaction, thereby obtaining a hydrazine compound represented by the formula (2). Further, when the obtained hydrazine compound is oxidized with an oxidizing agent, such as $PbO_2$, $KMnO_4$ or $CrO_3$, there is obtained a hydrazyl radical represented by the formula (1). More specifically, for example, 2,2-diphenyl-1-picrylhydrazine can be obtained by heating under reflux a mixture of diphenylhydrazine, picryl chloride and sodium hydrogencarbonate in an ethanol solvent and, then, crystallizing the resultant with benzene-ethanol. 2,2-Diphenyl-1-picrylhydrazyl can be obtained by oxidizing the obtained 2,2-diphenyl-1-picrylhydrazine with $PbO_2$ in a benzene solvent in the presence of sodium sulfate, wherein the $PbO_2$ is used in a molar amount which is 10 to 20 times the molar amount of the hydrazine. Other hydrazine compounds and hydrazyl radicals can be easily prepared by the above-mentioned method using respective corresponding materials. (With respect to the details of production methods of hydrazine compounds and hydrazyl radicals, reference can be made to, for example, Tetrahedron, 13, 258, 1961, J. Phys. Chem. 65, 710, 1961, Can. J. Chem. 58, 723, 1980, and Revue Roumaine de Chimie, 46(4), 363, 2001.)

The oxidation promoter, which is optionally used in the present invention, promotes an oxidation reaction when added to the reaction system together with the at least one member selected from the group consisting of a hydrazyl radical represented by the formula (1) and a hydrazine compound represented by the formula (2). As an oxidation promoter, there can be used various types of metals including the metal elements of Groups 1 to 16 of the Periodic Table. An oxidation promoter may be used in the form of a metal oxide, a metal salt, or an organometal compound. However, it is preferred that an oxidation promoter is a metal compound which contains at least one metal element selected from the group of transition metal elements. As transition metal elements of the transition metal compounds, at least one element selected from the elements of Groups 3 to 12 of the Periodic Table is preferred. Among the elements of Group 3, preferred are lanthanoids, such as La, Ce, Sm, Eu, Ac and Th. Among the elements of Group 4, preferred are Ti, Zr and Hf. Among the elements of Group 5, preferred are V, Nb and Ta. Among the elements of Group 6, preferred are Cr, Mo and W. Among the elements of Group 7, preferred are Mn and Re. Among the elements of Group 8, preferred are Fe, Ru and Os. Among the elements of Group 9, preferred are Co, Rh and Ir. Among the elements of Group 10, preferred are Ni, Pd and Pt. Among the elements of Group 11, preferred are Cu, Ag and Au. Among the elements of Group 12, preferred are Zn and Cd.

Examples of transition metal compounds include inorganic metal compounds, such as simple substances of the above-mentioned transition metal elements, hydroxides, oxides (including compound oxides), halides (a fluoride, a chloride, a bromide and an iodide), oxoacid salts (e.g., a nitrate, a sulfate, a phosphate, a borate, a perchlorate and a carbonate), oxoacids and polyacids (isopoly acids and heteropoly acids); and or ganometal compounds, such as organic salts (e.g., an acetate, a propionate, a thiocyanate, a naphthenate and a stearate) and complexes. As ligands which form the above-mentioned complexes, there can be mentioned hydroxyl, alkoxyl, acyl, alkoxycarbonyl, acetylacetonato, cyclopentadienyl, a halogen atom, carbonyl, an oxygen atom; and compounds, such as $H_2O$ (aquo), phosphine, CN, NO, $NO_2$, $NO_3$, $NH_3$ (amine), ethylenediamine, pyridine and phenanthroline. The above-mentioned metal compounds can be used individually or in combination. Further, the above-mentioned metal elements or metal compounds may be used in the form of a salt or a complex with the oxidation catalyst of the present invention (comprising hydrazyl radical of formula (1) and/or hydrazine compound of formula (2)).

Specific examples of transition metal compounds include tungsten compounds, such as metal tungsten, tungsten oxide, tungsten oxytetrachloride, tungstic acid, sodium tungstate, zinc tungstate, cobalt tungstate, cesium tungstate, tungsten hexacarbonyl, tungsten pentaethoxide, tungsten hexaphenoxide, silicotungstate, metatungstate, phosphotungstate, cobalt tungstate, molybdenum tungstate, manganese tungstate and manganese molybdenum tungstate.

Examples of titanium compounds include metal titanium, titanium oxide, titanium tetrachloride, titanium(II) sulfate, (acetylacetonato)titanium oxide, titanium tetraethoxide, titanium tetra-iso-propoxide, titaniumu tetra-iso-butoxide, titanium naphthenate, titanium silicalite molecular sieves, titanium phosphate, zirconium titanate, sodium titanate and barium titanate.

Further, examples of molybdenum compounds include metal molybdenum, molybdenum oxide, molybdenum chloride, molybdenum 2-ethylhexanate, molybdenum hexacarbonyl, bis(acetylacetonato) molybdenum oxide, molybdic acid, sodium molybdate, molybdophosphate, molybdosilicate, cobalt molybdate, manganese molybdate, vanadomolybdophosphate, manganese vanadium molybdate and manganese vanadium molybdophosphate. As compounds of other metal elements, there can be mentioned compounds corresponding to the above-mentioned tungsten compounds, titanium compounds and molybdenum compounds.

Transition metal compounds may be homogenous or heterogeneous, and may be a heterogeneous solid wherein metal components are carried on an appropriate carrier. As examples of carriers, there can be mentioned activated carbon, $SiO_2$, $Al_2O_3$, $SiO_2/Al_2O_3$, $TiO_2$, $ZrO_2$, ZnO, barium sulfate, potassium carbonate, silious earth and zeolite. As a method for preparing an oxidation promoter in which metal components are carried on a carrier, there can be mentioned methods used for producing conventional carrier-supported catalysts, for example, an absorption method, an impregnation method, a coprecipitation method and a sol-gel method. The amount of metal components carried on a carrier is from 0.0001 to 0.8 part by weight, preferably from 0.001 to 0.5 part by weight, more preferably from 0.01 to 0.3 part by weight, relative to 1 part by weight of the carrier.

The amount of an oxidation promoter is generally from 0.00005 to 0.8 mole, preferably from 0.0001 to 0.4 mole, still more preferably from 0.0005 to 0.2 mole, per mole of the substrate.

The amount ratio (molar ratio) of hydrazyl radical of formula (1) and/or hydrazine compound of formula (2) (referred to as "oxidation catalyst" below) to an oxidation promoter (i.e., "oxidation catalyst/oxidation promoter" molar ratio) is generally from 99/1 to 1/99, preferably from 90/10 to 10/90, still more preferably from 80/20 to 20/80.

The "Periodic Table" used herein is that prescribed in the IUPAC (International Union of Pure and Applied Chemistry) nomenclature system of inorganic chemistry (1989).

Examples of substrates which can be used in the oxidation reaction method of the present invention include various substrates which can be used in the selective oxidation reactions explained above under "Prior Art", such as hydrocarbons, alcohols, carbonyl compounds, ethers, amines, sulfur compounds and heterocyclic compounds. Oxidation products are as follows: from hydrocarbons, there can be obtained alcohols, aldehydes, ketones, epoxy compounds, carboxylic acids, peroxides and the like; from alcohols, there can be obtained aldehydes, ketones, carboxylic acids, peroxides and the like; from carbonyl compounds, there can be obtained carboxylic acids, peroxides and the like; from ethers, there can be obtained esters, acid anhydrides and the like; from amines, there can be obtained Schiff bases, nitriles, oximes, nitro compounds, hydroxylamines, nitrones, N-oxides and the like; from sulfur compounds, there can be obtained disulfides, sulfonic acids, sulfoxides and the like; and from heterocyclic compounds, there can be obtained N-oxides, sulfoxides and the like.

The above-mentioned substrates may be substituted with various substituents, such as an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxy group, an aryloxy group, a haloalkyl group, a mercapto group, an alkylthio group, an arylthio group, a sulfo group, a sulfinyl group, a sulfonyl group or a heterocyclic group.

Specific examples of hydrocarbons include unsaturated or saturated, linear or branched aliphatic hydrocarbons, such as propane, n-butane, isobutane, n-pentane, n-hexane, 2-methylpentan, 3-methylpentan, propylene, 2-butene, isobutene, butadiene, isoprene, 1-pentene, 1-hexene, 1-heptene, 3-methyl-1-butene, 2,3-dimethyl-1-butene and allyl chloride; unsaturated or saturated alicyclic hydrocarbons, such as cyclopentane, cyclohexane, cycloheptane, cyclooctane, methylcyclohexane, ethylcyclohexane, dimethylcyclohexane, chlorocyclohexane, methoxycyclohexane, cyclopentene, cyclohexene, cyclooctene, cyclopentadiene, cyclohexadiene, cyclooctadiene, dicyclopentadiene, adamantane, limonene and terpinene; and aromatic hydrocarbons such as benzene, toluene, xylene, ethylbenzene, propylbenzene, cumene, styrene, diphenylmethane, triphenylmethane, bibenzyl, stilbene, indene, naphthalene, tetralin and anthracene.

Specific examples of alcohols include unsaturated or saturated aliphatic alcohols, such as methanol, ethanol, n-propanol, isopropanol, n-butanol, s-butanol, t-butanol, n-pentanol, n-hexanol, n-heptanol, allyl alcohol and crotyl alcohol; unsaturated or saturated alicyclic alcohols, such as cyclopentanol, cyclohexanol, cycloheptanol, methylcyclohexanol, cyclohexene-1-ol; aliphatic or alicyclic polyhydric alcohols, such as ethylene glycol, propylene glycol, trimethylene glycol, 1,3-butanediol, 1,2-cyclohexanediol and 1,4-cyclohexanediol; and aromatic alcohols, such as benzyl alcohol, salicyl alcohol and benzhydrol.

The term "carbonyl compound" means a compound which has at least one carbonyl group in a molecule thereof. Specific examples of carbonyl compounds include aldehydes, such as formaldehyde, acetaldehyde, propionaldehyde, butyraldehyde, isobutyraldehyde, 1-pentanal, 1-hexnal, 1-heptanal, 1-octanal, 1-nonanal, 1-decanal, acrolein, methacrolein, benzaldehyde, nitrobenzaldehyde, aminobenzaldehyde, glutaraldehyde, adipaldehyde; and ketones, such as acetone, methylethylketone, methylpropylketone, methylisopropylketone, methylbutylketone, methylisobutylketone, cyclopentanone, cyclohexanone, cyclooctanone, cyclododecanone, 2-methylcyclohexanone, 2-ethylcyclohexanone, 2,6-dimethylcyclohexanone, acetophenone, propiophenone, benzophenone, 4-chloroacetophenone and 1-acetonaphthone.

Specific examples of ethers include diethyl ether, dipropyl ether, diisopropyl ether, dibutyl ether, methylethyl ether, methylbutyl ether, ethylbutyl ether, diallyl ether, methyl vinyl ether, anisole, dibenzyl ether and phenyl benzyl ether.

Specific examples of amines include aliphatic amines, such as methylamine, dimethylamine, trimethylamine, ethylamine, diethylamine, triethylamine, propylamine, dipropylamine, tripropylamine, isopropylamine, diisopropylamine, butylamine, dibutylamine, tributylamine, allylamine, diallylamine and triallylamine; alicyclic amines, such as cyclopentylamine, cyclohexylamine, cycloheptylamine and cyclooctylamine; and aromatic amines, such as aniline, N-methylaniline, N,N-dimethylaniline, toluidine, benzylamine and phenylenediamine.

Specific examples of sulfur compounds include thiols, such as methanethiol, ethanethiol, 1-propanethiol, 1-butanethiol, 1-hexanethiol, 1-octanethiol, ethylene thioglycol, propylene thioglycol, cyclopentanthiol, cyclohexanethiol, methylcyclohexanethiol, phenylmethanethiol and 2-phenylethanethiol; and sulfides, such as diethyl sulfide, dipropyl sulfide, diisopropyl sulfide, dibutyl sulfide, methyl ethyl sulfide, methyl butyl sulfide, ethyl butyl sulfide, diallyl sulfide, methyl phenyl sulfide, ethyl phenyl sulfide, diphenyl sulfide and dibenzyl sulfide.

Specific examples of heterocyclic compounds include furan, thiophene, pyrrole, thiopyran, pyridine, piperidine, morpholine, thiazole, imidazole, pyrimidine, 1,3,5-triazine, indole, quinoline, purine, chroman, carbazol, benzothiazole and benzoisoquinoline.

The above-mentioned substrates may be used individually or in combination. Further, it is not necessarily that a substrate be purified. A substrate may be used in the form of a mixture with other organic or inorganic compounds.

In the present invention, as a substrate, amines are preferred.

As amines used in the present invention, a primary amine and a secondary amine are preferred. With respect to the primary amines used in the present invention, there is no particular limitation as long as the primary amine has a structure wherein an amino group has a substituent bonded thereto through a carbon atom thereof, wherein the carbon atom through which the substituent is bonded to the amino group has at least one hydrogen atom bonded thereto. The primary amine contains one or more of such an amino group in the molecule thereof.

An example of the primary amine explained above is a compound represented by formula (9) below.

[Ka 21]

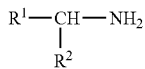

(9)

wherein each of $R^1$ and $R^2$ independently represents a hydrogen atom, an aliphatic group, an aromatic group or an aralkyl group, provided that $R^1$ and $R^2$ are not simultaneously hydrogen atoms; and
wherein $R^1$ and $R^2$ are optionally bonded to each other, to thereby form a ring.

The aliphatic group mentioned above represents an unsaturated or saturated, linear or branched aliphatic hydrocarbon group, or an unsaturated or saturated, alicyclic hydrocarbon group. Further, the above-mentioned aliphatic group, aromatic group and aralkyl group may be substituted with a substituent, such as an aliphatic group, an aromatic group, an aralkyl group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group. Examples of rings formed by bonding $R^1$ and $R^2$ include a cyclopentane ring, a cyclohexane ring, a cycloheptane ring and a cyclododecane ring. In general, the aliphatic group has 1 to 20 carbon atoms, preferably 1 to 15 carbon atoms, more preferably 1 to 10 carbon atoms; the aromatic group has 5 to 12 carbon atoms, preferably 6 to 10 carbon atoms; and the aralkyl group has 1 to 20 carbon atoms, preferably 1 to 15 carbon atoms.

Specific examples of such primary amines include methylamine, ethylamine, n-propylamine, n-butylamine, n-pentylamine, n-hexylamine, n-heptylamine, n-octylamine, n-nonylamine, n-decylamine, isopropylamine, isobutylamine, sec-butylamine, 1-methylbutylamine, 2-methylbutylamine, cyclopentylamine, cyclohexylamine, cyclododecylamine, benzylamine, 4-methylbenzylamine, 1-methylbenzylamine, 1-phenylethylamine, 3-aminomethylpyridine, 1-(4-chlorophenyl)ethylamine, 1-(3-methoxyphenyl)ethylamine, 1-(4-trifluoromethylphenyl)ethylamine, 1-phenylpropylamine, 1-naphthylethylamine and 1,6-hexanediamine. Further examples of primary amines include an optically active amine having an asymmetric carbon atom in the molecule thereof and a primary amine salt of an acid (such as hydrochloric acid, sulfuric acid or nitric acid).

When a primary amine is contacted with a molecular oxygen in the presence of the oxidation catalyst of the present invention, there is obtained an oxime compound or a nitro compound, each of which is formed by the oxidation of an amino group of the primary amine.

When a primary amine represented by formula (9) above is subjected to oxidation reaction using the oxidation catalyst of the present invention, there is obtained an oxime compound represented by formula (11) below or a nitro compound represented by formula (12) below.

[Ka 22]

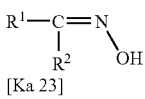

(11)

[Ka 23]

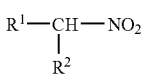

(12)

wherein $R^1$ and $R^2$ are as defined above formula (9).

Specific examples of oxime compounds include formaldehyde oxime, acetoaldehyde oxime, propionaldehyde oxime, n-butylaldehyde oxime, n-pentylaldehyde oxime, n-hexylaldehyde oxime, n-heptylaldehyde oxime, n-octylaldehyde oxime, n-nonylaldehyde oxime, n-decylaldehyde oxime, acetone oxime, methyl ethyl ketone oxime, sec-butylaldehyde oxime, isopentylaldehyde oxime, 1-methyl propyl ketone oxime, 2-methylbutylaldehyde oxime, cyclobutanone oxime, cyclopentanone oxime, cyclohexanone oxime, cyclododecanone oxime, benzaldehyde oxime, acetophenone oxime, phenylacetoaldehyde oxime, 4-chloroacetophenone oxime, 3-methoxyphenylacetophenone oxime, 2,4-dichloroacetophenone oxime, 4-trifluoromethylacetophenone oxime, phenyl ethyl ketone oxime, phenyl isopropyl ketone oxime and phenyl (4-methylphenyl)methyl ketone oxime.

Specific examples of nitro compounds include nitromethane, nitroethane, 1-nitropropane, 1-nitrobutane, 1-nitropentane, 1-nitrohexane, 1-nitroheptane, 1-nitropropane, 2-nitrobutane, 3-methyl-1-nitrobutane, 1-methyl-1-nitrobutane, 2-methyl-1-nitrobutane, nitrocyclobutane, nitrocyclopentane, nitrocyclohexane, nitrocyclododecane, phenylnitromethane, 1-phenyl-1-nitroethane, 2-phenyl-1-nitroethane, 1-(4-chlorophenyl)-1-nitroethane, 1-(3-methoxyphenyl)-1-nitroethane, 1-(2,4-dichlorophenyl)-1-nitroethane, 1-(4-trifluoromethylphenyl)-1-nitroethane, 1-phenyl-1-nitropropane, 1-phenyl-2-(4-methylphenyl)-1-nitroethane and 1-(1-naphthyl)-1-nitroethane.

A primary amine which is especially preferred in the present invention is cyclohexylamine which generates cyclohexanone oxime as an oxidation product thereof.

With respect to the secondary amines used in the present invention, there is no particular limitation as long as the secondary amine has a structure wherein an amino group has two substituents bonded thereto each through a carbon atom thereof, wherein at least one of the two carbon atoms through which the two substituents are, respectively, bonded to the amino group has at least one hydrogen atom bonded thereto. The secondary amine contains one or more of such an amino group in the molecule thereof.

An example of the secondary amine explained above is a compound represented by formula (10) below.

[Ka 24]

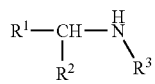

(10)

wherein each of $R^1$ and $R^2$ independently represents a hydrogen atom, an aliphatic group, an aromatic group or an aralkyl group, and $R^3$ has the same definition as each of $R^1$ and $R^2$ except that $R^3$ does not represent a hydrogen atom; and wherein two substituents selected from the group consisting of $R^1$, $R^2$ and $R^3$ are optionally bonded to each other, to thereby form a ring.

The aliphatic group mentioned above represents an unsaturated or saturated, linear or branched aliphatic hydrocarbon group, or an unsaturated or saturated, alicyclic hydrocarbon group. Further, the above-mentioned aliphatic group, aromatic group and aralkyl group may be substituted with a substituent, such as an aliphatic group, an aromatic group, an aralkyl group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxy group, an aryloxy group, a haloalkyl group, a mercapto group, an alkylthio group, an arylthio group, a sulfo group, sulfinyl group, a sulfonyl group or a heterocyclic group. Examples of rings formed by bonding two substituents selected from the group consisting of $R^1$, $R^2$ and $R^3$ include a cyclopentane ring, a cyclohexane ring, a cycloheptane ring, a cyclododecane ring, a pyrrolidine ring, a pyperidine ring and a tetrahydroisoquinoline ring. In general, the aliphatic group has 1 to 20 carbon atoms, preferably 1 to 15 carbon atoms, more preferably 1 to 10 carbon atoms; the aromatic group has 5 to 12 carbon atoms, preferably 6 to 10 carbon atoms; and the aralkyl group has 1 to 20 carbon atoms, preferably 1 to 15 carbon atoms.

Specific examples of such secondary amines include N,N-dimethylamine, N,N-diethylamine, N,N-di-(n-propyl)amine, N,N-di-(n-butyl)amine, N,N-di-(n-pentyl)-amine, N,N-di-(n-hexyl)amine, N,N-di-(n-heptyl)amine, N,N-di-(n-octyl)amine, N,N-di-(n-nonyl)amine, N,N-di-(n-decyl)amine, N,N-diisopropylamine, N,N-isobutylamine, N,N-di-(sec-butyl)amine, N-ethyl-tert-butylamine, N,N-dibenzylamine, N-benzyl-tert-butylamine, N-benzylaniline, 1,2,3,4-tetrahydroquinoline, 6,7-methylenedioxy-1,2,3,4-tetrahydroisoquinoline, pyrrolidine, 2-methylpyrrolidine, 2-carbomethoxypyrrolidine, 3,4-dimethoxypyrrolidine, pyperidine, 2-methylpyperidine, 2-carbomethoxypyperidine and 2,6-dimethylpyperidine. Further examples of secondary amines include an optically active amine having an asymmetric carbon atom in the molecule thereof and a secondary amine salt with an acid (such as hydrochloric acid, sulfuric acid or nitric acid).

When a secondary amine is contacted with a molecular oxygen in the presence of the oxidation catalyst of the present invention, there is obtained a nitrone compound which is formed by the oxidation of an amino group of the secondary amine.

When a secondary amine represented by formula (10) above is subjected to oxidation reaction using the oxidation catalyst of the present invention, there is obtained a nitrone compound represented by formula (13) below.

[Ka 25]

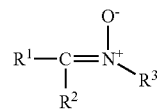

(13)

wherein $R^1$, $R^2$ and $R^3$ are as defined above for formula (10).

Specific examples of nitrone compounds include N-methylidenemethylamine N-oxide, N-ethylidenemethylamine N-oxide, N-propylidenemethylamine N-oxide, N-butylidenebutylamine N-oxide, N-pentylideneamylamine N-oxide, N-octylideneoctylamine N-oxide, N-nonylidenenonylamine N-oxide, N-decylidenedecylamine N-oxide, N-dodecylidenedodecylamine N-oxide, N-isopropylideneisopropylamine N-oxide, N-isobutylideneisobutylamine N-oxide, N-sec-butylidene-sec-butylamine N-oxide, N-isoamilideneisoamylamine N-oxide, N-ethylidene-tert-butylamine N-oxide, N-benzylidenebenzylamine N-oxide, N-benzylidene-tert-butylamine N-oxide, N-benzylideneaniline N-oxide, 3,4-dihydroisoquinoline N-oxide, 6,7-methylenedioxy-3,4-dihydroisoquinoline N-oxide, 3,4-dihydroisoquinoline N-oxide, 6,7-methylenedioxy-3,4-dihydroisoquinoline N-oxide, 1-pyrroline N-oxide, 2-methyl-1-pyrroline N-oxide, 2-carbomethoxy-1-pyrroline N-oxide, 3,4-dimethoxy-1-pyrroline N-oxide, 2,3,4,5-tetrahydropyridine N-oxide, 2-methyl-2,3,4,5-tetrahydropyridine N-oxide, 2-carbomethoxy-2,3,4,5-tetrahydropyridine N-oxide and 2,6-dimethyl-2,3,4,5-tetrahydropyridine N-oxide.

In the method of the present invention, when the oxidation reaction of the secondary amine is performed in the presence of an acceptor for a nitrone compound (the oxidation product), especially an olefin, it becomes possible to directly synthesize an addition product of the nitrone compound. The nitrone compound obtained by the method of the present invention is an excellent 1,3-dipole which undergoes an addition reaction with various olefins, to thereby generate a 1,3-dipole adduct. Such a dipole adduct is a precursor for physiological substances, such as an alkaloid, and is a very useful compound. Therefore, in the present invention, it is commercially very advantageous to perform the oxidation reaction of a secondary amine in the presence of an olefin.

In the present invention, the oxidation reaction may be performed in either the liquid phase or the gaseous phase, and a liquid phase is preferred. Specifically, when the oxidation reaction is performed in the liquid phase, the oxidation reaction is either performed in a reaction medium which is at least one member selected from the group consisting of water and an organic solvent, or performed using the substrate as a reaction medium.

The term "organic solvent" means either a protic organic solvent or an aprotic organic solvent. Examples of protic solvents include organic carboxylic acids, such as a primary, secondary or tertiary $C_1$-$C_{10}$ alcohol (e.g., methanol, ethanol, isopropyl alcohol or t-butyl alcohol), formic acid, acetic acid and propionic acid. Examples of aprotic solvents include aliphatic hydrocarbons, such as hexane and octane; aromatic hydrocarbons, such as benzene and toluene; halogenated hydrocarbons, such as chloroform, dichloromethane, carbon tetrachloride and chlorobenzene; nitriles, such as acetonitrile, propionitrile and benzonitrile; nitro compounds, such as nitrobenzene, nitromethane and nitroethane; ethers, such as dimethylether, diethylether, diisopropylether and dioxane; esters, such as ethylacetate and butylacetate; and amides, such as formamide, acetoamide, dimethylformamide, dimethylacetoamide, diethylacetoamide and hexamethylphosphoric triamide. In the oxidation reaction performed by the method of the present invention, use of an aprotic solvent is preferred. Especially, nitriles, nitro compounds, esters, ethers and amides are preferred, and more preferred are are nitriles, such as acetonitrile and benzonitrile, and amides, such as dimethylformamide and dimethylacetoamide.

The above-mentioned solvents can be used individually or in combination. When the oxidation reaction is performed in the presence of water and/or an organic solvent, the concentration of a substrate is generally in the range of from 0.1 to 95% by weight, preferably from 1 to 30% by weight, based on the total weight of the water and/or the organic solvent and the substrate.

In the method of the present invention for performing an oxidation reaction, the oxidation reaction is performed by contacting a substrate with a molecular oxygen in the presence of an oxidation catalyst. The reaction may be performed by a fixed-bed process or a suspension-bed process and in any conventional manner of reaction, such as a batchwise manner, a semi-batchwise manner or a continuous manner. In general, the molecular oxygen is purified oxygen, air or a gaseous mixture of oxygen and an inert gas, such as nitrogen or helium. When a gaseous mixture of oxygen and an inert gas is used as the molecular oxygen, it is preferred that the oxygen concentration of the gaseous mixture is in the range of from 2 to 23% by volume, more advantageously from 3 to 11% by volume; however, it is preferred that the oxygen concentration is in a range such that the resultant gaseous phase does not have an explosive composition.

In the method of the present invention, it is preferred that the oxidation of a substrate is performed in the liquid phase. Therefore, it is required that the molecular oxygen (which has been introduced as a gas into the reaction system) be dissolved in a desired concentration in the liquid phase containing the catalyst, under the conditions for the oxidation. However, for example, when a molecular oxygen (hereinafter, frequently referred to as a "molecular oxygen-containing gas") is introduced into the reaction system under reduced pressure or atmospheric pressure and at a temperature at which a liquid reaction mixture containing the substrate, the reaction product and/or the solvent is refluxed, only a very small amount of oxygen can be dissolved in the liquid phase. Therefore, for achieving a desired concentration of oxygen dissolved in the liquid phase, it is preferred to use a method in which the molecular oxygen-containing gas is contacted with the liquid phase under superatmospheric pressure (which is not more than 20 MPa).

With respect to the total pressure of the reaction system, for example, when it is intended to perform the oxidation in a batchwise manner by using a gaseous mixture of oxygen and an inert gas, the oxidation may be performed by introducing a gaseous mixture having an appropriate oxygen concentration and an appropriate total pressure into the reaction system, wherein the oxygen concentration and the total pressure are determined, taking into consideration the amount of the substrate to be oxidized (i.e., the amount of oxygen needed to oxidize the substrate) which varies depending on the type of catalyst and the reaction conditions. In general, the total pressure of the reaction system is in the range of from 0.1 to 20 MPa, preferably from 1 to 10 MPa.

With respect to the method for introducing the molecular oxygen-containing gas into the reaction system, there is no particular limitation. For example, the molecular oxygen-containing gas may be introduced either directly into the liquid phase which is formed in the reaction vessel, or into the gaseous phase (which is in contact with the liquid phase) in the reaction vessel.

The molecular oxygen consumed in the reaction can be compensated by introducing purified oxygen, air or diluted oxygen gas into the reaction system either continuously or intermittently, so as to maintain a desired partial pressure of oxygen in the gaseous phase. Alternatively, when the oxidation is performed in a batchwise manner, by introducing an oxygen-containing gas into the reaction system, which gas contains oxygen in an amount sufficient for oxidizing a desired amount of the substrate, it becomes possible to continue the reaction without compensating for the consumed molecular oxygen until a desired conversion is achieved.

In the method of the present invention, it is preferred that the reaction temperature is generally in the range of from 0 to 200° C., more advantageously from 40 to 180° C., most advantageously from 60 to 160° C. Although the reaction temperature depends on the chemical reaction performed, when the temperature exceeds 200° C., a gradual decomposition or gradual oxidation of the obtained product is promoted and a by-product having a high boiling point is formed in a higher ratio, thus lowering the selectivity for the desired product. On the other hand, when the temperature is lower than 0° C., the reaction rate tends to become low.

The reaction time is not particularly limited and can be appropriately selected in accordance with the desired values of the selectivity for and yield of the desired product. Usually, the reaction time is selected from the range of from several seconds to several hours.

From the reaction mixture obtained by the reaction, the reaction product can be easily separated and purified by conventional methods, for example, separation methods, such as a distillation, an extraction, a condensation, a filtration, a crystal deposition, a recrystallization, a column chromatography or a combination of two or more separation methods. Generally, it is preferred that the unreacted substrate is recycled to the reaction vessel. When the catalyst is contained in the reaction medium after separating the reaction product, such reaction medium may be recycled to the reaction vessel and reused for the oxidation reaction.

Next, the reaction mechanism of the oxidation reaction using the oxidation catalyst of the present invention is explained below, taking as an example a reaction for producing cyclohexanone oxime from cyclohexylamine and oxygen.

A hydrazyl radical represented by formula (1) is used as an oxidation catalyst of the present invention, and a specific example of a hydrazyl radical of formula (1) is a free radical, such as 2,2-diphenyl-1-picrylhydrazyl (DPPH), which removes a hydrogen atom from chemical linkages (such as C—H, N—H, PhO—H and S—H) of an organic substrate, to thereby selectively produce a corresponding radical species. In the reaction between DPPH and an organic substrate, DPPH itself is transformed into 2,2-diphenyl-1-picrylhydrazine ($DPPH_2$); that is, in the reaction between DPPH and an organic substrate, DPPH functions as a receptor for a hydrogen radical. This reaction has been known for a long time and it is applied to a stoichiometric coupling reaction and the like (see, for example, Can. J. Chem. 39, 1588, 1961). The present inventor has found that, when the hydrazyl radical represented by formula (1), which has the above-mentioned reaction characteristics, is contacted with a substrate in the presence of a molecular oxygen, the hydrazyl radical functions as a catalyst, thereby enabling production of a desired oxidation product under moderate conditions with high selectivity and in high yield. The same effects can also be obtained by using, as an oxidation catalyst, a hydrazine compound represented by formula (2) or a mixture of a hydrazyl radical represented by formula (1) and a hydrazine compound represented by formula (2).

The functional mechanism of the catalyst system of the present invention has not yet been fully elucidated. However, it is presumed that DPPH and $DPPH_2$ function as a hydrogen mediator while undergoing reversible mutual transformation. More specifically, it is presumed that the following catalyst cycle is established in the reaction system: $DPPH_2$ is generated in the reaction system by a reaction between a substrate and DPPH; the generated $DPPH_2$ directly activates an oxygen molecule to thereby generate an electrophilic oxygen active species and DPPH; and the generated DPPH pulls out a hydrogen atom from a reaction intermediate which is formed by addition of an oxygen molecule to the substrate, thereby regenerating $DPPH_2$.

During the course of the studies by the present inventor, the present inventor analyzed the functional mechanism of the catalyst system by using as a model the reaction of DPPH with N-cyclohexylhydroxylamine which is presumed to be a reaction intermediate of an oximation reaction of cyclohexylamine. As a result, it became apparent that the reaction represented by formula (i) below proceeds stoichiometrically in the reaction system. Further, it was found that, when the reaction represented by formula (i) below is performed in the presence of $WO_3/Al_2O_3$ (alumina having supported thereon tungsten oxide) (oxidation promoter) under high oxygen pressure conditions, DPPH functions like a catalyst in the reaction system. It was also found that, even when $DPPH_2$ is used instead of DPPH, the reaction proceeds in a catalytic manner. These results obtained from the analyses performed by the present inventor suggest that DPPH and $DPPH_2$ function as a hydrogen mediator while undergoing reversible mutual transformation, and that the activation of oxygen molecules (such as the reaction represented by formula (ii) below) is efficiently performed by using the substrate as a hydrogen source. That is, it is presumed that $DPPH_2$ causes a reduction of an oxygen molecule; then, the resultant oxygen molecule in a reduced form generates an oxygen active species on the metal atom of the oxidation promoter; and, then, the oxygen active species participates in the oxidation reaction of the substrate. It is known that the oxidative activity of the oxygen active species, which is generated on the metal atom of the oxidation promoter, varies depending on the metal compound used as the oxidation promoter. Therefore, in the reaction system of the present invention, the oxidation reaction can be controlled as desired by selecting an appropriate oxidation promoter in accordance with the type of the substrate used and the type of the desired oxidation product. For example, as demonstrated in Examples 14 and 15 below, in the oxidation reaction of cyclohexylamine, each of cyclohexanone oxime and nitrocyclohexane can be produced selectively by changing the type of the oxidation promoter used.

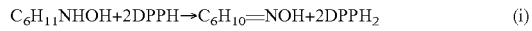

(i)

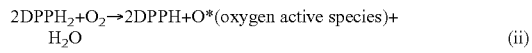

(ii)

As explained above, each of the hydrazyl radical represented by formula (1) (such as DPPH) and the hydrazine compound represented by formula (2) (such as $DPPH_2$) functions as a catalyst in the oxidation reaction of an organic substrate in the presence of oxygen. From electrochemical experiments, it has conventionally been known that DPPH and DPPH2 can undergo reversible mutual transformation (see, for example, Electrochemistry Communications, 1, 406 (1999)); however, it has not been reported that, in the presence of oxygen, DPPH and $DPPH_2$ exhibit a catalytic function as a hydrogen mediator while undergoing reversible mutual transformation. As mentioned above, the hydrazyl radical represented by formula (1), such as a DPPH radical, has the ability to pull out a hydrogen radical from various organic substrates. Therefore, the oxidation catalyst of the present invention can be applied to oxygen oxidation reaction of various organic substrates.

BEST MODE FOR CARRYING OUT THE INVENTION

Hereinbelow, the present invention will be described in more detail with reference to the following Examples and Comparative Examples, which should not be construed as limiting the scope of the present invention.

In the Examples and Comparative Examples, various properties were measured and evaluated as follows.

1) Conversion of a Substrate and Selectivity for an Oxidation Product

The conversion of a substrate and the selectivity for an oxidation product, which were used for evaluating the results of the oxidation reaction of a substrate in the Examples and Comparative Examples, are defined by the following formulae, respectively.

Conversion of a substrate (%)=(molar amount of a reacted substrate/molar amount of fed substrate)×100

Selectivity for an oxidation product (%)=(molar amount of an oxidation product/molar amount of a reacted substrate)×100

The reaction product was analyzed by gas chromatography under the following conditions.

Apparatus: gas chromatograph Model GC-14A, manufactured and sold by Shimadzu Corporation, Japan (including a flame ionization detector (FID))

Column: capillary column DB-1701, manufactured and sold by J&W Scientific, U.S.A. (0.25 mm×30 m)

Carrier gas: helium

Flow rate: 20 ml/min

Analysis mode: maintained at 50° C. for 10 min; then, temperature-elevated to 280° C. at a rate of 10° C./min; and, then, maintained at 280° C. for 5 min.

2) Determination of the Amounts of Metals Contained in the Oxidation Promoter (Solid Powdery Product)

The amounts of metals contained in the solid powdery product were determined by means of an X-ray fluorescence analyzer under the following conditions.

Apparatus: RIX-3000, manufactured and sold by Rigaku Corporation, Japan (X-Ray Excitation Conditions)

Target Element: Rh

Tube voltage: 50 kV

Tube current: 50 mA

Single crystal used for a monochromator: polyethylene terephthalate for the determination of Al and Si, and lithium fluoride for the determination of other metals Detector: scintillation counter (Preparation of Samples)

A predetermined amount of the solid powdery product was mixed and diluted with a crystalline cellulose (as a binder) to obtain a powder mixture (solid powdery product/crystalline cellulose (weight ratio)=1/2 to 1/3), and the obtained powder mixture was formed into tablets under a pressure of 20 tons by using a tableting machine in which the powder mixture was held by an aluminum ring (as a mold).

(Preparation of the Calibration Curve)

With respect to each of the metal oxides used in the oxidation promoter, tablets (standard samples) containing the metal oxide were produced in substantially the same manner as mentioned above, except that, instead of the oxidation promoter, different amounts of the metal oxide were, respectively, used for producing the tablets. The obtained tablets were analyzed by X-ray fluorescence spectrometry, thereby obtaining a calibration curve for determination of the metal contents of the oxidation promoter.

The chemical formulae of the oxide catalysts used in Examples 1 to 32 are shown below.

[Ka 26]

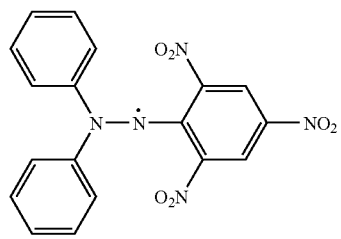

(a)

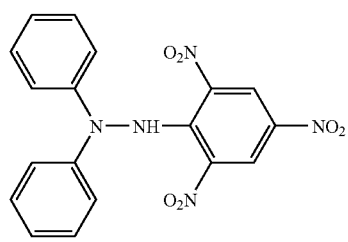

(b)

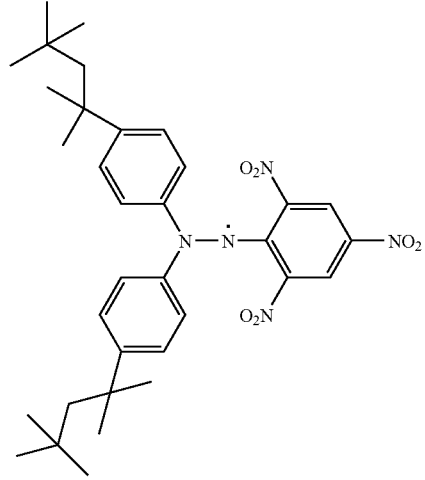

(c)

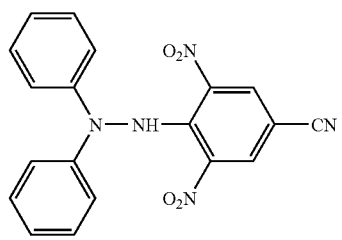

(d)

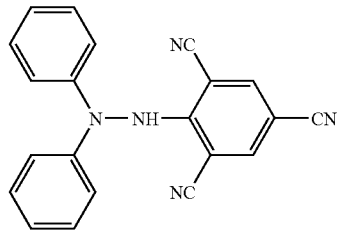

(e)

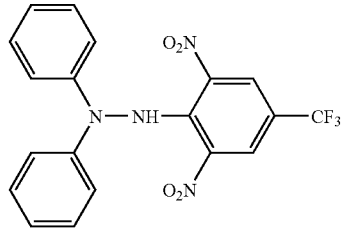

(f)

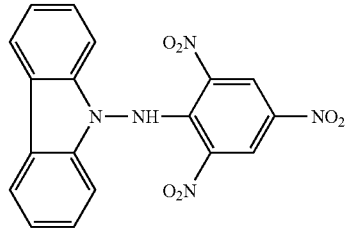

(g)

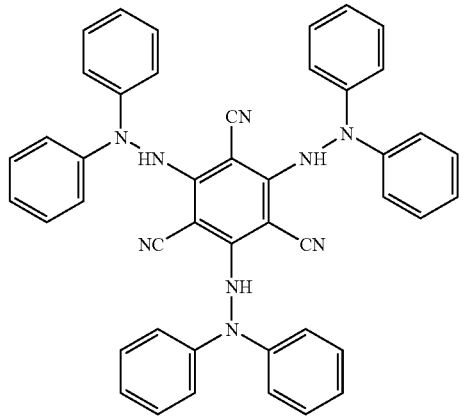

(h)

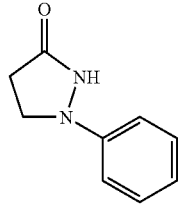

(i)

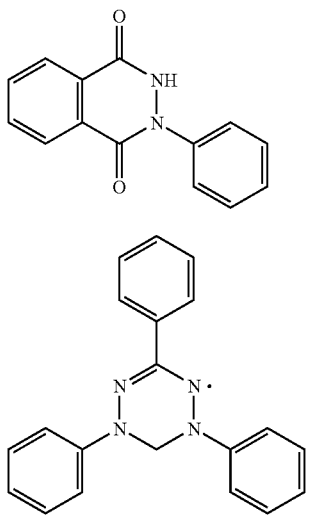

The nomenclatures of the compounds above are listed below. Compounds (d) to (h) were synthesized in accordance with a conventional method (for example, a method described in Tetrahedron, 24, 1063, 1968; or Revue Roumaine de Chimie, 46(4), 363, 2001). With respect to other compounds, commercially available products were used.

[Nomenclatures of Hydrazyl Radicals and Hydrazine Compounds]
(a) 2,2-diphenyl-1-picrylhydrazyl
(b) 2,2-diphenyl-1-picrylhydrazine
(c) 2,2-di(4-tart-octylphenyl)-1-picrylhydrazyl
(d) 2,2-diphenyl-1-(4-cyano-2,6-dinitrophenyl)hydrazine
(e) N,N-diphenyl-N'-(2,4,6-tricyanophenyl)hydrazine
(f) 2,2-diphenyl-1-(2,6-dinitro-4-fluoromethylphenyl)hydrazine
(g) carbazol-9-yl-(2,4,6-trinitrophenyl)amine
(h) 1,3,5-tris(N,N-diphenylhydrazino)-2,4,6-tricyanobenzol
(i) 1-phenyl-pyrazolidin-3-one
(j) 1-phenyl-1,2-dihydro-pyridazine-3,6-dione
(k) 2,4,6-triphenyl-3,4-dihydro-2H-[1,2,4,5]tetrazin-1-yl Example 1

Preparation of an Oxidation Promoter 100 g of a commercially available aluminum s-butoxide was placed in a glass beaker. Then, into the beaker was dropwise charged an aqueous solution of ammonium metatungstate (which had been prepared by dissolving 7.0 g of commercially available ammonium metatungstate in 100 g of water) while vigorously stirring by means of a glass rod. The resultant gel-like product was air-dried at room temperature for 1 hour, followed by vacuum-drying at 120° C. overnight. The resultant dried product was subjected to calcination treatment in a furnace at 400° C. for 4 hours under atmospheric pressure while feeding air into the furnace, thereby obtaining a solid powdery product (oxidation promoter) comprised of alumina having supported thereon tungsten oxide ($WO_3/Al_2O_3$). The obtained oxidation promoter was examined by X-ray fluorescence spectrometry. As a result, it was found that the oxidation promoter had a tungsten content of 21.8% by weight.

(Oxidation Reaction of Cyclohexylamine)

Next, 0.049 g (0.125 mmol) of 2,2-diphenyl-1-picrylhydrazyl (i.e., DPPN) (manufactured and sold by Sigma-Aldrich Japan K.K., Japan) as an oxidation catalyst, 0.1 g of the above-prepared $WO_3/Al_2O_3$ (oxidation promoter), 3 ml of acetonitrile as a solvent and 0.496 g (5 mmol) of cyclohexylamine as a substrate were charged into a high pressure autoclave having an internal volume of 120 ml, which was made of stainless steel SUS 316 and was equipped with a magnetic stirrer. After closing the autoclave, the inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 5 MPa. Then, the autoclave was secured to an oil bath, and the mixture in the autoclave was heated to 80° C., followed by an oxidation reaction at a reaction temperature of 80° C. for 4 hours while stirring, to thereby produce cyclohexanone oxime.

After cooling the autoclave, the residual pressure was removed therefrom, and the autoclave was opened. The resultant reaction mixture having dispersed therein the catalyst was recovered from the autoclave and diluted with ethanol. The diluted reaction mixture was subjected to a filtration to thereby remove the catalyst and obtain a filtrate. The obtained filtrate was analyzed by gas chromatography.

As a result, it was found that the cyclohexylamine conversion was 58.9%, and the selectivity for cyclohexanone oxime was 94.9%. Further, decomposition of 2,2-diphenyl-1-picrylhydrazyl was not observed even after the reaction and, therefore, it was confirmed that this oxidation catalyst is stable during the oxidation reaction.

Example 2

An oxidation reaction was performed in substantially the same manner as in Example 1 except that the reaction time was changed to 8 hours. As a result, it was found that the conversion of cyclohexylamine was 80.3% and the selectivity for cyclohexanone oxime was 93.0%.

Example 3

An oxidation reaction was performed in substantially the same manner as in Example 1 except that 0.049 g (0.125 mmol) of 2,2-diphenyl-1-picrylhydrazine (manufactured and sold by Sigma-Aldrich Japan K.K., Japan) was used as an oxidation catalyst instead of the oxidation catalyst used in Example 1. As a result, it was found that the conversion of cyclohexylamine was 40.7% and the selectivity for cyclohexanone oxime was 95.7%.

Example 4

An oxidation reaction was performed in substantially the same manner as in Example 1 except that a mixture of 0.024 g (0.06 mmol) of 2,2-diphenyl-1-picrylhydrazyl and 0.026 g (0.065 mmol) of 2,2-diphenyl-1-picrylhydrazine was used as an oxidation catalyst instead of the oxidation catalyst used in Example 1. As a result, it was found that the conversion of cyclohexylamine was 53.1% and the selectivity for cyclohexanone oxime was 95.2%.

Example 5

An oxidation reaction was performed in substantially the same manner as in Example 1 except that 0.077 g (0.125 mmol) of 2,2-di(4-t-octylphenyl)-1-picrylhydrazyl (manufactured and sold by Sigma-Aldrich Japan K.K., Japan) was used as an oxidation catalyst instead of the oxidation catalyst used in Example 1. As a result, it was found that the conversion of cyclohexylamine was 62.4% and the selectivity for cyclohexanone oxime was 95.6%.

Example 6

An oxidation reaction was performed in substantially the same manner as in Example 1 except that 0.047 g (0.125 mmol) of 2,2-diphenyl-1-(4-cyano-2,6-dinitrophenyl)hydrazine was used as an oxidation catalyst instead of the oxidation catalyst used in Example 1. As a result, it was found that the conversion of cyclohexylamine was 45.1% and the selectivity for cyclohexanone oxime was 91.4%.

Example 7

An oxidation reaction was performed in substantially the same manner as in Example 1 except that 0.042 g (0.125 mmol) of N,N-diphenyl-N'-(2,4,6-tricyanophenyl)hydrazine was used as an oxidation catalyst instead of the oxidation catalyst used in Example 1. As a result, it was found that the conversion of cyclohexylamine was 41.2% and the selectivity for cyclohexanone oxime was 93.0%.

Example 8

An oxidation reaction was performed in substantially the same manner as in Example 1 except that 0.052 g (0.125 mmol) of 2,2-diphenyl-1-(2,6-dinitro-4-fluoromethylphenyl)hydrazine was used as an oxidation catalyst instead of the oxidation catalyst used in Example 1. As a result, it was found that the conversion of cyclohexylamine was 50.1% and the selectivity for cyclohexanone oxime was 89.0%.

Example 9

An oxidation reaction was performed in substantially the same manner as in Example 1 except that 0.049 g (0.125 mmol) of carbazol-9-yl(2,4,6-trinitrophenyl)amine was used as an oxidation catalyst instead of the oxidation catalyst used in Example 1. As a result, it was found that the conversion of cyclohexylamine was 43.2% and the selectivity for cyclohexanone oxime was 94.5%.

Example 10

An oxidation reaction was performed in substantially the same manner as in Example 1 except that 0.087 g (0.125 mmol) of 1,3,5-tris(N,N-diphenylhydrazino)-2,4,6-tricyanobenzol was used as an oxidation catalyst instead of the oxidation catalyst used in Example 1. As a result, it was found that the conversion of cyclohexylamine was 60.1% and the selectivity for cyclohexanone oxime was 92.7%.

Example 11

An oxidation reaction was performed in substantially the same manner as in Example 1 except that 0.041 g (0.25 mmol) of 1-phenylpyrazolidine-3-one (manufactured and sold by Wako Pure Chemical Industries, Ltd., Japan) was used as an oxidation catalyst instead of the oxidation catalyst used in Example 1. As a result, it was found that the conversion of cyclohexylamine was 30.2% and the selectivity for cyclohexanone oxime was 86.2%.

Example 12

An oxidation reaction was performed in substantially the same manner as in Example 1 except that 0.047 g (0.25 mmol) of 1-phenyl-1,2-dihydropyridazine-3,6-dione (manufactured and sold by Wako Pure Chemical Industries, Ltd., Japan) was used as an oxidation catalyst instead of the oxidation catalyst used in Example 1. As a result, it was found that the conversion of cyclohexylamine was 25.0% and the selectivity for cyclohexanone oxime was 84.1%.

Example 13

An oxidation reaction was performed in substantially the same manner as in Example 1 except that 0.079 g (0.25 mmol) of 2,4,6-triphenyl-3,4-dihydro-2H-[1,2,4,5]tetrazine-1-yl (manufactured and sold by Sigma-Aldrich Japan K.K., Japan) was used as an oxidation catalyst instead of the oxidation catalyst used in Example 1. As a result, it was found that the conversion of cyclohexylamine was 20.5% and the selectivity for cyclohexanone oxime was 83.7%.

Example 14

An oxidation reaction was performed in substantially the same manner as in Example 1 except that the oxidation promoters indicated in Table 1 below were individually used in the concentrations mentioned below. With respect to the oxidation promoters indicated in Table 1, the following should be noted. $WO_3/Al_2O_3$ (i.e., alumina having supported thereon tungsten oxide) was prepared in the same manner as in Example 1; $WO_3/ZrO_2$ (i.e., zirconium having supported thereon tungsten oxide) and $WO_3/TiO_2$ (i.e., titanium oxide having supported thereon tungsten oxide) were individually prepared by the methods explained below; and the below-mentioned commercially available products were individually used as the other oxidation promoters: $TiO_2$ (P25; manufactured and sold by Degussa AG, Germany), $TiO_2$-mesopore (manufactured and sold by Sigma-Aldrich Japan K.K., Japan), W-ETS-10 (manufactured and sold by N.E. Chemcat Corporation, Japan), $Ti(Oi-Pr)_4$ (manufactured and sold by Wako Pure Chemical Industries, Ltd., Japan), $TiO(acac)_2$ (manufactured and sold by Wako Pure Chemical Industries, Ltd., Japan), and $Nb_2O_5$-mesopore (manufactured and sold by Sigma-Aldrich Japan K.K., Japan) (wherein "$TiO(acac)_2$" stands for titanium(II) oxide acetylacetonate which is represented by the formula: $TiO(CH_3COCHCOCH_3)_2$; and "$Ti(Oi-Pr)_4$" stands for titanium tetraisopropoxide which is represented by the formula: $Ti[OCH(CH_3)_2]_4$). The amount of the oxidation promoter was the same as in Example 1, namely 0.1 g, except that each of $Ti(Oi-Pr)_4$ and $TiO(acac)_2$ was used in an amount of 0.125 mmol. The obtained products were individually analyzed by gas chromatography. As shown in Table 1, cyclohexanone oxime was selectively obtained by using different oxidation promoters.

(Preparation of $WO_3/ZrO_2$)

A commercially available $ZrO_2$ (RC100; manufactured and sold by DAIICHI KIGENSO KAGAKU KOGYO CO., LTD., Japan) was dried at 120° C. overnight, and the dried $ZrO_2$ was used as a carrier for an oxidation promoter. 1.4 g of ammonium paratungstate pentahydrate was dissolved in 60 g of water, followed by addition of 10 g of the dried $ZrO_2$, to thereby obtain a suspension.

The obtained suspension was charged into a glass flask, and the flask was set in a rotary evaporator. The flask attached to the rotary evaporator was immersed in an oil bath having a temperature of 90° C., and the contents of the flask were slowly stirred under atmospheric pressure for 1.5 hours, to thereby obtain a slurry. The temperature of the oil bath was elevated from 90° C. to 100° C., and the slurry in the flask was stirred at 100° C. under atmospheric pressure to evaporate water from the slurry in the flask, thereby obtain a dry powder. The obtained dry powder was further dried at 120° C. overnight and, then, a predetermined amount of the powder was charged into a glass tubular furnace and calcined at 500° C. for 4 hours under atmospheric pressure while feeding air into the furnace, thereby obtaining a solid powdery product comprised of $ZrO_2$ having supported thereon tungsten oxide ($WO_3/ZrO_2$). The obtained solid powdery product was examined by X-ray fluorescence spectrometry. As a result, it was found that the solid powdery product had a tungsten content of 9.2% by weight.

(Preparation of $WO_3/TiO_2$)

Substantially the same procedure as in the above-mentioned method for preparing $WO_3/ZrO_2$ was repeated except that $TiO_2$ (P25; manufactured and sold by Degussa AG, Germany) was used as a carrier instead of $ZrO_2$, thereby obtaining a solid powdery product ($WO_3/TiO_2$). The obtained solid powdery product was examined by X-ray fluorescence spectrometry. As a result, it was found that the solid powdery product had a tungsten content of 9.5% by weight.

TABLE 1

| Oxidation promoter | Conversion of amine (%) | Selectivity for oxime (%) |
| --- | --- | --- |
| $WO_3/Al_2O_3$ | 58.9 | 94.9 |
| $WO_3/ZrO_2$ | 62.8 | 86.0 |
| $WO_3/TiO_2$ | 22.3 | 63.6 |
| $TiO_2$ | 35.7 | 89.9 |
| $TiO_2$-mesopore | 32.4 | 87.8 |
| $H^+$-ETS-10 | 13.9 | 92.7 |
| Ti(Oi-Pr)$_4$ | 67.2 | 87.8 |
| TiO(acac)$_2$ | 60.5 | 89.3 |
| $Nb_2O_5$-mesopore | 50.1 | 79.6 |

Example 15

An oxidation reaction was performed in substantially the same manner as in Example 1 except that the oxidation promoters indicated in Table 2 below were individually used in the concentrations mentioned below. The below-mentioned commercially available products were individually used as the oxidation promoters: $WO_3$ (manufactured and sold by Wako Pure Chemical Industries, Ltd., Japan), $Na_2WO_4.2H_2O$ (manufactured and sold by Wako Pure Chemical Industries, Ltd., Japan), $H_2WO_4$ (manufactured and sold by Wako Pure Chemical Industries, Ltd., Japan), $Na_2MoO_4.2H_2O$ (manufactured and sold by Wako Pure Chemical Industries, Ltd., Japan), $MoO_2(acac)_2$ (manufactured and sold by Wako Pure Chemical Industries, Ltd., Japan), and $Mo(CO)_6$ (manufactured and sold by Wako Pure Chemical Industries, Ltd., Japan) (wherein "$MoO_2(acac)_2$" stands for molybdenum oxide bis(acetylacetonate) which is represented by the formula: $MoO_2(CH_3COCHCOCH_3)_2$). Each of these oxidation promoters was used in an amount of 0.125 mmol, except that $WO_3$ was used in an amount of 0.1 g. The obtained products were individually analyzed by gas chromatography. As shown in Table 2, nitrocyclohexane was selectively obtained by using different oxidation promoters.

TABLE 2

| Oxidation promoter | Conversion of amine (%) | Selectivity for nitrocyclohexane (%) |
| --- | --- | --- |
| $WO_3$ | 9.1 | 62.3 |
| $Na_2WO_4.2H_2O$ | 13.3 | 55.6 |
| $H_2WO_4$ | 28.3 | 50.8 |
| $Na_2MoO_4.2H_2O$ | 7.0 | 72.7 |
| $MoO_2(acca)_2$ | 9.5 | 68.6 |
| $Mo(CO)_6$ | 11.8 | 57.4 |

Example 16

An oxidation reaction was performed in substantially the same manner as in Example 1 except that 0.125 mmol of $Na_2MoO_4.2H_2O$ (manufactured and sold by Wako Pure Chemical Industries, Ltd., Japan) was used as an oxidation promoter instead of the oxidation promoter used in Example 1, and that the amount of 2,2-diphenyl-1-picrylhydrazyl was changed to 0.2 g (0.5 mmol). As a result, it was found that the conversion of cyclohexylamine was 29.3% and the selectivity for nitrocyclohexane was 79.1%.

Example 17

An oxidation reaction was performed in substantially the same manner as in Example 16 except that the reaction temperature was changed to 90° C. As a result, it was found that the conversion of cyclohexylamine was 62.5% and the selectivity for nitrocyclohexane was 76.3%.

Example 18

An oxidation reaction was performed in substantially the same manner as in Example 1 except that various solvents as indicated in Table 3 below were individually used instead of the solvent used in Example 1. The obtained products were individually analyzed by gas chromatography. As shown in Table 3, cyclohexanone oxime was selectively obtained by using different solvents.

TABLE 3

| Solvent | Conversion of amine (%) | Selectivity for oxime (%) |
| --- | --- | --- |
| 1,4-dioxane | 11.6 | 88.8 |
| benzene | 6.3 | 84.3 |
| chlorobenzene | 4.1 | 95.8 |
| pyridine | 6.5 | 82.7 |
| ethylacetate | 41.2 | 93.8 |
| nitrobenzene | 46.8 | 96.5 |
| benzonitrile | 42.1 | 94.2 |
| acetonitrile | 58.9 | 94.9 |
| dimethylformamide | 76.5 | 96.6 |
| dimethylacetoamide | 46.4 | 95.2 |
| water | 5.1 | 83.4 |
| methanol | 14.4 | 90.9 |
| t-butanol | 8.6 | 92.5 |

Example 19

An oxidation reaction was performed in substantially the same manner as in Example 1 except that 3 ml of dimethylformamide was used as a solvent instead of the solvent used in Example 1, and that the reaction time was changed to 9 hours. As a result, it was found that the conversion of cyclohexylamine was 95.1% and the selectivity for cyclohexanone oxime was 96.3%.

Example 20

An oxidation reaction was performed using various reaction systems in which different primary amines as indicated in Table 4 below were individually used as a substrate and in which the substrate was used as a solvent (reaction medium). The reaction was performed in substantially the same manner as in Example 1 except that 0.03 g (0.075 mmol) of 2,2-diphenyl-1-picrylhydrazyl (manufactured and sold by Sigma-Aldrich Japan K.K., Japan) as an oxidation catalyst, 0.1 g of $WO_3/Al_2O_3$ (oxidation promoter) and 30 mmol of each individual primary amine (as a substrate and solvent) as indicated in Table 4 below were charged into a high pressure autoclave. The obtained products were individually analyzed by gas chromatography. As shown in Table 4, an oxime corresponding to each primary amine used was selectively obtained.

TABLE 4

| Primary amine | Conversion of amine (%) | Selectivity for oxime (%) |
| --- | --- | --- |
| n-butylamine | 9.3 | 61.8 |
| sec-butylamine | 4.5 | 92.3 |
| n-hexylamine | 9.3 | 70.8 |
| n-octylamine | 7.5 | 73.1 |
| cyclopentylamine | 24.0 | 78.5 |
| cyclohexylamine | 22.1 | 89.0 |
| cyclooctylamine | 10.3 | 87.9 |
| benzylamine | 30.4 | 51.3 |
| 4-methylbenzylamine | 27.3 | 51.5 |
| 3-aminomethylpyridine | 16.7 | 47.5 |
| 1-phenylethylamine | 12.6 | 63.4 |

Example 21

An oxidation reaction was performed in substantially the same manner as in Example 1 except that the reaction conditions, such as reaction temperature, oxygen pressure and reaction time were changed as indicated in Table 5 below. The obtained products were individually analyzed by gas chromatography. As shown in Table 5, cyclohexanone oxime was selectively obtained under different reaction conditions.

TABLE 5

| Reaction conditions | | | Conversion of amine (%) | Selectivity for oxime (%) |
| --- | --- | --- | --- | --- |
| Temperature (° C.) | Oxygen pressure (MPa) | Time (hr) | | |
| 60 | 5 | 2 | 5.4 | 97.5 |
| 80 | 5 | 2 | 20.8 | 97.9 |
| 90 | 5 | 2 | 40.0 | 94.8 |
| 100 | 5 | 2 | 59.3 | 92.7 |
| 110 | 5 | 2 | 85.2 | 89.8 |
| 80 | 3 | 4 | 47.5 | 94.9 |
| 80 | 5 | 4 | 58.9 | 94.9 |
| 80 | 10 | 4 | 83.2 | 93.0 |

Example 22

An oxidation reaction was performed in substantially the same manner as in Example 1 except that the amounts of oxidation catalyst (DPPH) and oxidation promoter ($WO_3/Al_2O_3$) were changed as indicated in Table 6 below, and that the reaction time was changed to 2 hours. The obtained products were individually analyzed by gas chromatography. As shown in Table 6, cyclohexanone oxime was selectively obtained by using various amounts of DPPH and $WO_3/Al_2O_3$.

TABLE 6

| Reaction conditions | | Conversion of amine (%) | Selectivity for oxime (%) |
| --- | --- | --- | --- |
| DPPH (mmol) | $WO_3/Al_2O_3$ (g) | | |
| 0 | 0.1 | 0 | 0 |
| 0.125 | 0.1 | 20.8 | 97.9 |
| 0.25 | 0.1 | 46.0 | 95.0 |
| 0.375 | 0.1 | 66.9 | 94.7 |
| 0.125 | 0 | 3.2 | 40.6 |
| 0.125 | 0.02 | 11.9 | 93.4 |
| 0.125 | 0.05 | 19.0 | 95.6 |
| 0.125 | 0.1 | 20.8 | 97.9 |
| 0.125 | 0.2 | 18.6 | 95.1 |

Example 23

An oxidation reaction was performed in substantially the same manner as in Example 1 except that 0.646 g (5 mmol) of dibutylamine (manufactured and sold by Sigma-Aldrich Japan K.K., Japan) was used as a substrate instead of the substrate used in Example 1, and that the reaction time was changed to 8 hours. As a result, it was found that the conversion of dibutylamine was 43.5% and the selectivity for N-butylidenebutylamine-N-oxide was 72.1%.

Example 24

An oxidation reaction was performed in substantially the same manner as in Example 1 except that 0.986 g (5 mmol) of dibenzylamine (manufactured and sold by Sigma-Aldrich Japan K.K., Japan) was used as a substrate instead of the substrate used in Example 1, and that the reaction time was changed to 8 hours. As a result, it was found that the conversion of dibenzylamine was 49.5% and the selectivity for N-benzylidenebutylamine-N-oxide was 73.4%.

Example 25

An oxidation reaction was performed in substantially the same manner as in Example 1 except that 0.666 g (5 mmol) of 1,2,3,4-tetrahydroisoquinoline (manufactured and sold by Sigma-Aldrich Japan K.K., Japan) was used as a substrate instead of the substrate used in Example 1, and that the reaction time was changed to 8 hours. As a result, it was found that the conversion of 1,2,3,4-tetrahydroisoquinoline was 39.0% and the selectivity for 3,4-dihydroisoquinoline-N-oxide was 78.4%.

Example 26

An oxidation reaction was performed in substantially the same manner as in Example 1 except that 0.356 g (5 mmol) of pyrrolidine (manufactured and sold by Wako Pure Chemical Industries, Ltd., Japan) was used as a substrate instead of the substrate used in Example 1, and that the reaction time was changed to 8 hours. As a result, it was found that the conversion of pyrrolidine was 55.4% and the selectivity for 1-pyrroline-N-oxide was 65.3%.

Example 27

An oxidation reaction was performed in substantially the same manner as in Example 1 except that 0.426 g (5 mmol) of piperidine (manufactured and sold by Wako Pure Chemical Industries, Ltd., Japan) was used as a substrate instead of the substrate used in Example 1, and that the reaction time was changed to 8 hours. As a result, it was found that the conversion of piperidine was 48.3% and the selectivity for 2,3,4,5-tetrapyridine-N-oxide was 62.1%.

Example 28

An oxidation reaction was performed in substantially the same manner as in Example 1 except that 0.541 g (5 mmol) of benzyl alcohol (manufactured and sold by Wako Pure Chemical Industries, Ltd., Japan) was used as a substrate instead of the substrate used in Example 1, and that the reaction temperature was changed to 100° C. As a result, it was found that the conversion of benzyl alcohol was 15.4% and the selectivity for benzaldehyde was 99.0%.

Example 29

An oxidation reaction was performed in substantially the same manner as in Example 1 except that 0.5 g (5 mmol) of cyclohexanol (manufactured and sold by Wako Pure Chemical Industries, Ltd., Japan) was used as a substrate instead of the substrate used in Example 1, and that the reaction temperature was changed to 100° C. As a result, it was found that the conversion of cyclohexanol was 9.1% and the selectivity for cyclohexanone was 98.4%.

Example 30

An oxidation reaction was performed in substantially the same manner as in Example 1 except that, instead of the substrate, solvent and oxidation promoter used in Example 1, 0.5 g (5 mmol) of cyclohexanol (manufactured and sold by Wako Pure Chemical Industries, Ltd., Japan) was used as a substrate, 3 ml of dimethylformamide was used as a solvent, and 0.041 g (0.125 mmol) of $MoO_2(acac)_2$ (manufactured and sold by Wako Pure Chemical Industries, Ltd., Japan) was used as an oxidation promoter, and that the reaction temperature was changed to 100° C. As a result, it was found that the conversion of cyclohexanol was 14.3% and the selectivity for cyclohexanone was 97.2%.

Example 31

An oxidation reaction was performed in substantially the same manner as in Example 1 except that 0.451 g (5 mmol) of 1-butanethiol (manufactured and sold by Wako Pure Chemical Industries, Ltd., Japan) was used as a substrate instead of the substrate used in Example 1. As a result, it was found that the conversion of 1-butanethiol was 9.5% and the selectivity for butyldisulfide was 96.1%.

Example 32

An oxidation reaction was performed in substantially the same manner as in Example 1 except that, instead of the substrate, solvent and oxidation promoter used in Example 1, 0.451 g (5 mmol) of 1-butanethiol (manufactured and sold by Wako Pure Chemical Industries, Ltd., Japan) was used as a substrate, 3 ml of methanol was used as a solvent, and 0.066 g (0.2 mmol) of $Na_2WO_4.2H_2O$ (manufactured and sold by Wako Pure Chemical Industries, Ltd., Japan) was used as an oxidation promoter. As a result, it was found that the conversion of 1-butanethiol was 13.2% and the selectivity for butyldisulfide was 95.4%.

Comparative Example 1

An operation for effecting an oxidation reaction was performed in substantially the same manner as in Example 1 except that none of a hydrazyl radical and a hydrazine compound was used as an oxidation catalyst. As a result, the reaction did not proceed at all and, hence, no cyclohexanone oxime was obtained. Further, an operation for effecting an oxidation reaction was performed in substantially the same manner as in Example 1 except that benzylamine, N,N-dibutylamine, piperidine, benzyl alcohol and 1-butanethiol were individually used as a substrate instead of the substrate used in Example 1, and that none of a hydrazyl radical and a hydrazine compound was used as an oxidation catalyst. As a result, it was found that no oxidation product was obtained by the reaction.

Comparative Example 2

An oxidation reaction was performed in substantially the same manner as in Example 1 except that, instead of the oxidation catalyst used in Example 1, there was used 0.044 g (0.25 mmol) of p-trifluorophenylhydrazine (manufactured and sold by Sigma-Aldrich Japan K.K., Japan) having a structure different from that of the oxidation catalyst of the present invention. As a result, it was found that the conversion of cyclohexylamine was 4.2% and the selectivity for cyclohexanone oxime was 62.1%. It was also found that the amount of cyclohexanone oxime obtained was not more than the stoichiometric amount corresponding to the amount of hydrazine compound used, indicating that the hydrazine compound used in this Comparative Example 2 did not catalyze the oxidation unlike the oxidation catalyst of the present invention. Further, an oxidation reaction was performed in substantially the same manner as in Example 1 except that, instead of the oxidation catalyst used in Example 1, hydrazine monohydrate, 1,2-diphenylhydrazine, 2,4-dinitrophenylhydrazine, phthalic hydrazine and benzenesulfonylhydrazine were used individually as an oxidation catalyst. As a result, it was found that the amount of cyclohexanone oxime obtained was not more than the stoichiometric amount corresponding to the amount of hydrazine compound used, and that the selectivity for cyclohexanone oxime was as low as 50% or less. It was also found that the hydrazine compounds used in this Comparative Example 2 had been decomposed during the reaction.

Comparative Example 3

An oxidation reaction was performed in substantially the same manner as in Example 1 except that 0.039 g (0.25 mmol) of 2,2,6,6-tetramethylpiperidine-N-oxyl (TEMPO) (manufactured and sold by Sigma-Aldrich Japan K.K., Japan) was used as an oxidation catalyst instead of the oxidation catalyst used in Example 1. As a result, it was found that the conversion of cyclohexylamine was 2.9% and the selectivity for cyclohexanone oxime was 44.7%.

Comparative Example 4

An oxidation reaction was performed in substantially the same manner as in Example 1 except that 0.028 g (0.25 mmol)

of hydroquinone (manufactured and sold by Wako Pure Chemical Industries, Ltd., Japan) was used as an oxidation catalyst instead of the oxidation catalyst used in Example 1. As a result, it was found that the conversion of cyclohexylamine was 3.1% and the selectivity for cyclohexanone oxime was 54.3%.

Comparative Example 5

An oxidation reaction was performed in substantially the same manner as in Example 1 except that 0.082 g (0.5 mmol) of N-hydroxyphthalimide (manufactured and sold by Wako Pure Chemical Industries, Ltd., Japan) was used as an oxidation catalyst instead of the oxidation catalyst used in Example 1. As a result, it was found that the conversion of cyclohexylamine was 2.8 and the selectivity for cyclohexanone oxime was 79.6%.

Comparative Example 6

An oxidation reaction of cyclohexylamine was performed using hydrogen peroxide as an oxidizing agent, in accordance with the conventional techniques (e.g., U.S. Pat. No. 2,706,204) described under "Prior Art" above. Specifically, a reaction was performed as follows. Into a flask having a volume of 30 ml were charged 0.066 g (0.2 mmol) of $Na_2WO_4 \cdot 2H_2O$ (manufactured and sold by Wako Pure Chemical Industries, Ltd., Japan), 10 ml of methanol and 0.496 g (5 mmol) of cyclohexylamine, and the internal temperature of the flask was elevated to 30° C. Subsequently, 1.7 g (15 mmol) of a 30% aqueous solution of hydrogen peroxide was dropwise added to the contents of the flask. The resultant mixture in the flask was then subjected to reaction for 3 hours while stirring and maintaining the temperature of the flask at 30° C., to thereby obtain cyclohexanone oxime. As a result, it was found that the conversion of cyclohexylamine was 76.4 and the selectivity for cyclohexanone oxime was 79.2%.

The above-described results of the oximation of cyclohexylamine performed in each of Examples 1 to 14 and 18 to 22 and Comparative Example 6 show that, when an oxidation reaction of a substrate is performed by using the oxidation catalyst of the present invention and using a molecular oxygen as an oxidizing agent, advantages are obtained in that oxidation products can be produced with high selectivity and high efficiency, as compared to the case where hydrogen peroxide is used as an oxidizing agent.

INDUSTRIAL APPLICABILITY

As described hereinabove, by the use of the oxidation catalyst of the present invention, oxidation of various substrates with a molecular oxygen can be efficiently performed under moderate conditions, thereby enabling production of a useful chemical compound economically and safely with high selectivity.

The oxidation catalyst of the present invention can solve the various problems of the conventional processes for oxidation of a substrate, i.e., the problems that it is necessary to use an oxidizing agent which is expensive and/or explosive, that the selectivity for and yield of a desired compound become low, that complicated operations are necessary for purifying an oxidation product to remove therefrom a large amount of by-products, and that a large amount of energy is consumed.

The oxidation catalyst of the present invention can be advantageously used for performing selective oxidation reaction of various types of substrates, especially, e.g., a hydrocarbon, an alcohol, a carbonyl compound, an ether, an amine, a sulfur compound and a heterocyclic compound. For example, by the use of the oxidation catalyst of the present invention, selective oxidation reactions using a molecular oxygen to produce an oxime compound or a nitro compound from a primary amine or produce a nitrone compound from a secondary amine, can be performed without using an expensive oxidizing agent, such as hydrogen peroxide or an organic hydroperoxide and under moderate conditions with high selectivity and high efficiency.

The invention claimed is:

1. A method for producing a chemical compound, comprising contacting a substrate with molecular oxygen in the presence of an oxidation catalyst, thereby performing an oxidation reaction to form the chemical compound, said oxidation catalyst comprising at least one member selected from the group consisting of a hydrazyl radical represented by the formula (1) below and a hydrazine compound represented by the formula (2) below,

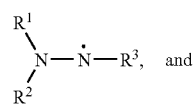

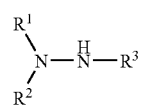

wherein each of $R^1$, $R^2$ and $R^3$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^3$ are optionally bonded to each other, to thereby form a ring.

2. The method according to claim 1, wherein said hydrazyl radical and said hydrazine compound are, respectively, represented by the following formulae (3) and (4):

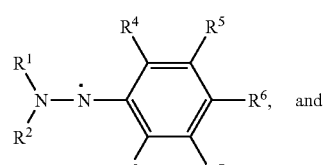

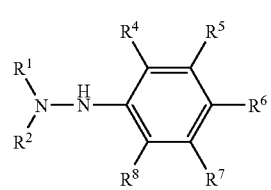

wherein each of $R^4$, $R^5$, $R^6$, $R^7$ and $R^8$ independently represents a hydrogen atom, an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atoms and groups;

each of $R^1$ and $R^2$ has the same definition as each of $R^4$ to $R^8$ except that $R^1$ and $R^2$ do not represent a hydrogen atom; and wherein $R^1$ and $R^2$ are optionally bonded to each other, to thereby form a ring, and wherein with respect to one or two pairs of substituents selected from the group consisting of a pair of substituents $R^4$ and $R^5$, a pair of substituents $R^5$ and $R^6$, a pair of substituents $R^6$ and $R^7$ and a pair of substituents $R^7$ and $R^8$, the substituents of the pair or of each pair are optionally bonded to each other, to thereby form a ring or two rings.

3. The method according to claim 1, wherein said hydrazyl radical is selected from the group consisting of 2,2-diphenyl-1-picrylhydrazyl, 2,2-diphenyl-1-(2,6-dinitro-4-fluoromethylphenyl)hydrazyl, 2,2-diphenyl-1-(4-cyano-2,6-dinitrophenyl)hydrazyl, N,N-diphenyl-N'-(2,4,6-tricyanophenyl)hydrazyl, 1,3,5-tris(N,N-diphenylhydrazyl)-2,4,6-tricyanobenzol, 2,2-di-(4-tert-octylphenyl)picrylhydrazyl, carbazol-9-yl(2,4,6-trinitrophenyl)amidogen and N-phenyl-N-(4-trifluoromethylphenyl)-N'-(2,4,6-trinitrophenyl)hydrazyl, and said hydrazine compound is selected from the group consisting of 2,2-diphenyl-1-picrylhydrazine, 2,2-diphenyl-1-(2,6-dinitro-4-fluoromethylphenyl)hydrazine, 2,2-diphenyl-1-(4-cyano-2,6-dinitrophenyl)hydrazine, N,N-diphenyl-N'-(2,4,6-tricyanophenyl)hydrazine, 1,3,5-tris(N,N-diphenylhydrazino)-2,4,6-tricyanobenzol, 2,2-di-(4-tert-octylphenyl)picrylhydrazine, carbazol-9-yl(2,4,6-trinitrophenyl)amine and N-phenyl-N-(4-trifluoromethylphenyl)-N'-(2,4,6-trinitrophenyl)hydrazine.

4. The method according to claim 1, wherein said hydrazyl radical is 2,2-diphenyl-1-picrylhydrazyl, and said hydrazine compound is 2,2-diphenyl-1-picrylhydrazine.

5. The method according to claim 1, wherein said hydrazyl radical and said hydrazine compound are, respectively, represented by the following formulae (5) and (6):

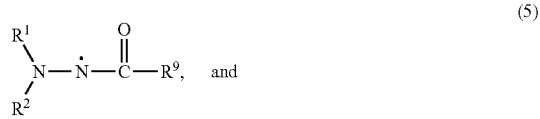

wherein each of $R^1$, $R^2$ and $R^9$ independently represents an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atom and groups; and wherein two substituents selected from the group consisting of $R^1$, $R^2$ and $R^9$ are optionally bonded to each other, to thereby form a ring.

6. The method according to claim 1, wherein said hydrazyl radical is selected from the group consisting of 1-phenylpyrazolidone-(3)-radical and 3,4-dihydro-1,4-dioxo-3-phenyl-2-phthalazinyl, and said hydrazine compound is selected from the group consisting of 1-phenylpyrazolidine-3-one, 1-phenyl-1,2-dihydropyridazine-3,6-dione and 2-phenyl-2,3-dihydrophthalazine-1,4-dione.

7. The method according to claim 1, wherein said hydrazyl radical and said hydrazine compound are, respectively, represented by the following formulae (7) and (8):

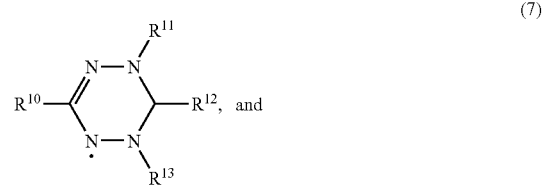

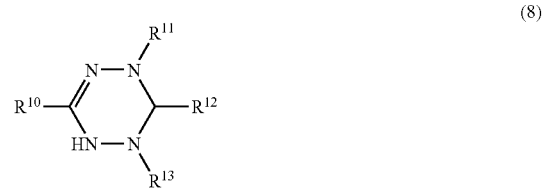

wherein each of $R^{10}$, $R^{11}$ and $R^{12}$ independently represents a hydrogen atom, an oxygen atom, a sulfur atom, an aliphatic group, an aromatic group, a halogen atom, a hydroxyl group, a nitro group, a nitroso group, a cyano group, an amino group, an imino group, an azo group, a carbonyl group, a carboxyl group, an acyl group, an alkoxycarbonyl group, an aryloxycarbonyl group, a carbamoyl group, an alkoxyl group, an aryloxy group, a haloalkyl group, a mercapto group, an alkylthio group, an arylthio group, a sulfo group, a sulfinyl group, a sulfonyl group or a heterocyclic group, or alternatively a group having two or more of these atoms and groups;

$R^{13}$ has the same definition as each of $R^{10}$ to $R^{12}$ except that $R^{13}$ does not represent a hydrogen atom; and wherein two substituents selected from the group consisting of $R^{11}$, $R^{12}$ and $R^{13}$ are optionally bonded to each other, to thereby form a ring.

8. The method according to claim 1, wherein said hydrazyl radical is selected from the group consisting of 2,4,6-triphenyl-3,4-dihydro-2H-[1,2,4,5]tetrazine-1-yl, 1,3,5,6-tetraphenylverdazyl, 1,3,5-triphenyl-6-oxoverdazyl and 1,3,5-triphenyl-6-thioxoverdazyl, and said hydrazine compound is selected from the group consisting of 2,4,6-triphenyl-1,2,3,4-tetrahydro-[1,2,3,4]tetrazine, 2,3,4,6-tetraphenyl-1,2,3,4-tetrahydro-[1,2,4,5]tetrazine, 1,3,5-triphenyl-6-oxotetrazine and 1,3,5-triphenyl-6-thioxotetrazine.

9. The method according to claim 1, wherein said oxidation catalyst further comprises an oxidation promoter, and said oxidation promoter is used in an amount of from 0.00005 to 0.8 mole per mole of said substrate.

10. The method according to claim 9, wherein said oxidation promoter is a transition metal compound.

11. The method according to claim 10, wherein said transition metal is at least one member selected from the group consisting of elements of Groups 3 to 12 of the Periodic Table.

12. The method according to claim 11, wherein said transition metal is at least one member selected from the group consisting of lanthanoids, Ti, Zr, Hf, V, Nb, Ta, Cr, Mo, W, Mn, Re, Fe, Ru, Os, Co, Rh, Ir, Ni, Pd, Pt, Cu, Ag, Au, Zn and Cd.

13. The method according to claim 1, wherein said substrate is selected from the group consisting of a hydrocarbon, an alcohol, a carbonyl compound, an ether, an amine, a sulfur compound and a heterocyclic compound.

14. The method according to claim 13, wherein said amine is a primary amine, and said chemical compound produced is an oxime compound or a nitro compound.

15. The method according to claim 14, wherein said primary amine is represented by the following formula (9):

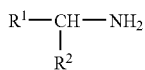
(9)

wherein each of $R^1$ and $R^2$ independently represents a hydrogen atom, an aliphatic group, an aromatic group or an aralkyl group, provided that $R^1$ and $R^2$ are not simultaneously hydrogen atoms; and wherein $R^1$ and $R^2$ are optionally bonded to each other, to thereby form a ring.

16. The method according to claim 15, wherein said primary amine is cyclohexylamine, and said chemical compound produced is cyclohexanone oxime.

17. The method according to claim 13, wherein said amine is a secondary amine, and said chemical compound produced is a nitrone compound.

18. The method according to claim 17, wherein said secondary amine is represented by the following formula (10):

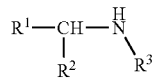
(10)

wherein each of $R^1$ and $R^2$ independently represents a hydrogen atom, an aliphatic group, an aromatic group or an aralkyl group, and $R^3$ has the same definition as each of $R^1$ and $R^2$ except that $R^3$ does not represent a hydrogen atom; and wherein two substituents selected from the group consisting of $R^1$, $R^2$ and $R^3$ are optionally bonded to each other, to thereby form a ring.

19. The method according to claim 1, wherein said oxidation reaction is either performed in at least one reaction medium selected from the group consisting of water and an organic solvent, or performed using said substrate as a reaction medium.

20. The method according to claim 19, wherein said organic solvent is an aprotic solvent.

21. The method according to claim 20, wherein said aprotic solvent is at least one member selected from the group consisting of a nitrile, a nitro compound, an ester, an ether and an amide.

22. The method according to claim 21, wherein said nitrile is at least one member selected from the group consisting of acetonitrile and benzonitrile.

23. The method according to claim 21, wherein said amide is at least one member selected from the group consisting of dimethylformamide and dimethylacetamide.

24. The method according to claim 1, wherein said at least one compound selected from the group consisting of the hydrazyl radical and the hydrazine compound is used in an amount of from 0.0001 to 1 mole per mole of said substrate.

25. The method according to claim 1, wherein said oxidation reaction is performed under reaction conditions wherein the temperature is from 0 to 200° C. and the pressure is from atmospheric pressure to 20 MPa.

* * * * *